US008340309B2

(12) United States Patent
Burnett et al.

(10) Patent No.: US 8,340,309 B2

(45) Date of Patent: Dec. 25, 2012

(54) NOISE SUPPRESSING MULTI-MICROPHONE HEADSET

(75) Inventors: Gregory C. Burnett, Dodge Center, MN (US); Jaques Gagne, Los Gatos, CA (US); Dore Mark, San Francisco, CA (US); Alexander M. Asseily, London (GB); Nicolas Petit, Burlingame, CA (US)

(73) Assignee: AliphCom, Inc., San Francisco, CA (US)

(*) Notice: Subject to any disclaimer, the term of this patent is extended or adjusted under 35 U.S.C. 154(b) by 1001 days.

(21) Appl. No.: 11/199,856

(22) Filed: Aug. 8, 2005

(65) Prior Publication Data

US 2006/0120537 A1 Jun. 8, 2006

Related U.S. Application Data

(60) Provisional application No. 60/599,468, filed on Aug. 6, 2004, provisional application No. 60/599,618, filed on Aug. 6, 2004.

(51) Int. Cl.

*G10K 11/16* (2006.01)
*H04B 15/00* (2006.01)
*A61F 11/06* (2006.01)

(52) U.S. Cl. ......................... 381/71.6; 381/94.7; 381/72

(58) Field of Classification Search .................... 381/72, 381/74, 312, 317, 328, 330, 94.7, 94.1, 71.5, 381/71.6; 704/214

See application file for complete search history.

(56) References Cited

U.S. PATENT DOCUMENTS

| | | | | |
|---|---|---|---|---|
| 4,972,468 | A * | 11/1990 | Murase et al. | 379/430 |
| 2002/0198705 | A1* | 12/2002 | Burnett | 704/214 |
| 2003/0128848 | A1* | 7/2003 | Burnett | 381/71.8 |
| 2004/0198462 | A1* | 10/2004 | Lee | 455/569.1 |
| 2005/0004796 | A1* | 1/2005 | Trump et al. | 704/225 |

* cited by examiner

*Primary Examiner* — Devona Faulk
*Assistant Examiner* — George Monikang
(74) *Attorney, Agent, or Firm* — Kokka & Backus, PC

(57) ABSTRACT

A new type of headset that employs adaptive noise suppression, multiple microphones, a voice activity detection (VAD) device, and unique mechanisms to position it correctly on either ear for use with phones, computers, and wired or wireless connections of any kind is described. In various embodiments, the headset employs combinations of new technologies and mechanisms to provide the user a unique communications experience.

27 Claims, 21 Drawing Sheets

FIG.1-A
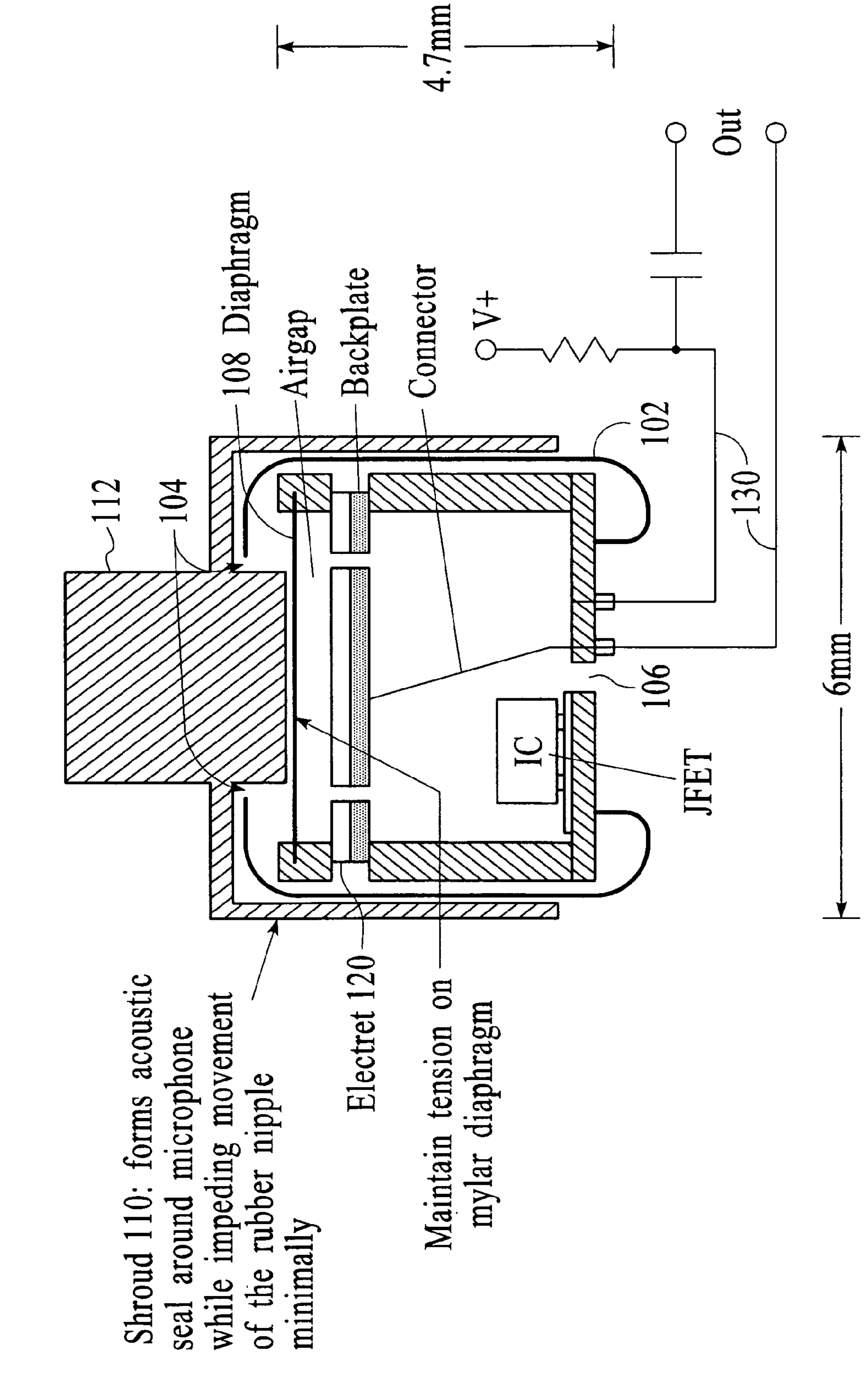

FIG.1-B

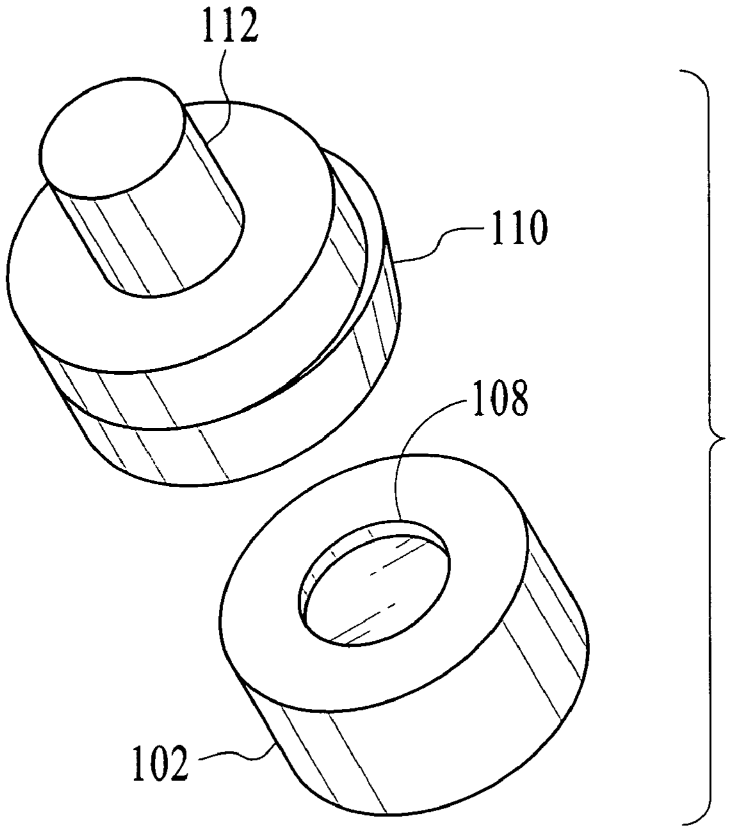
FIG.2A-A
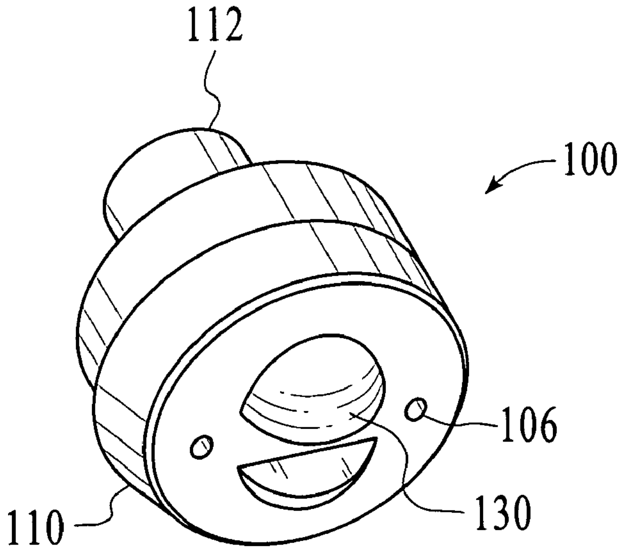
FIG.2B-A

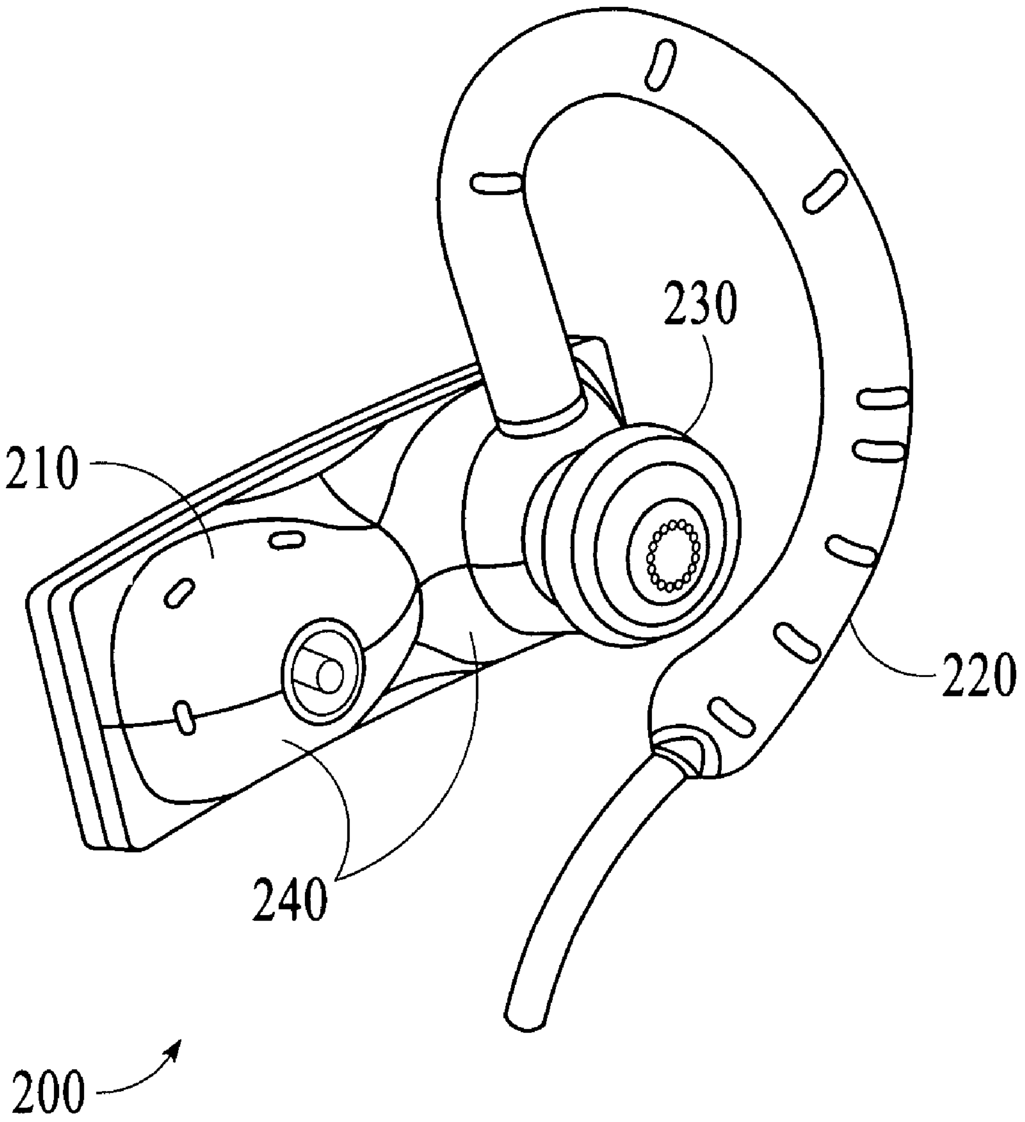
FIG.2-B

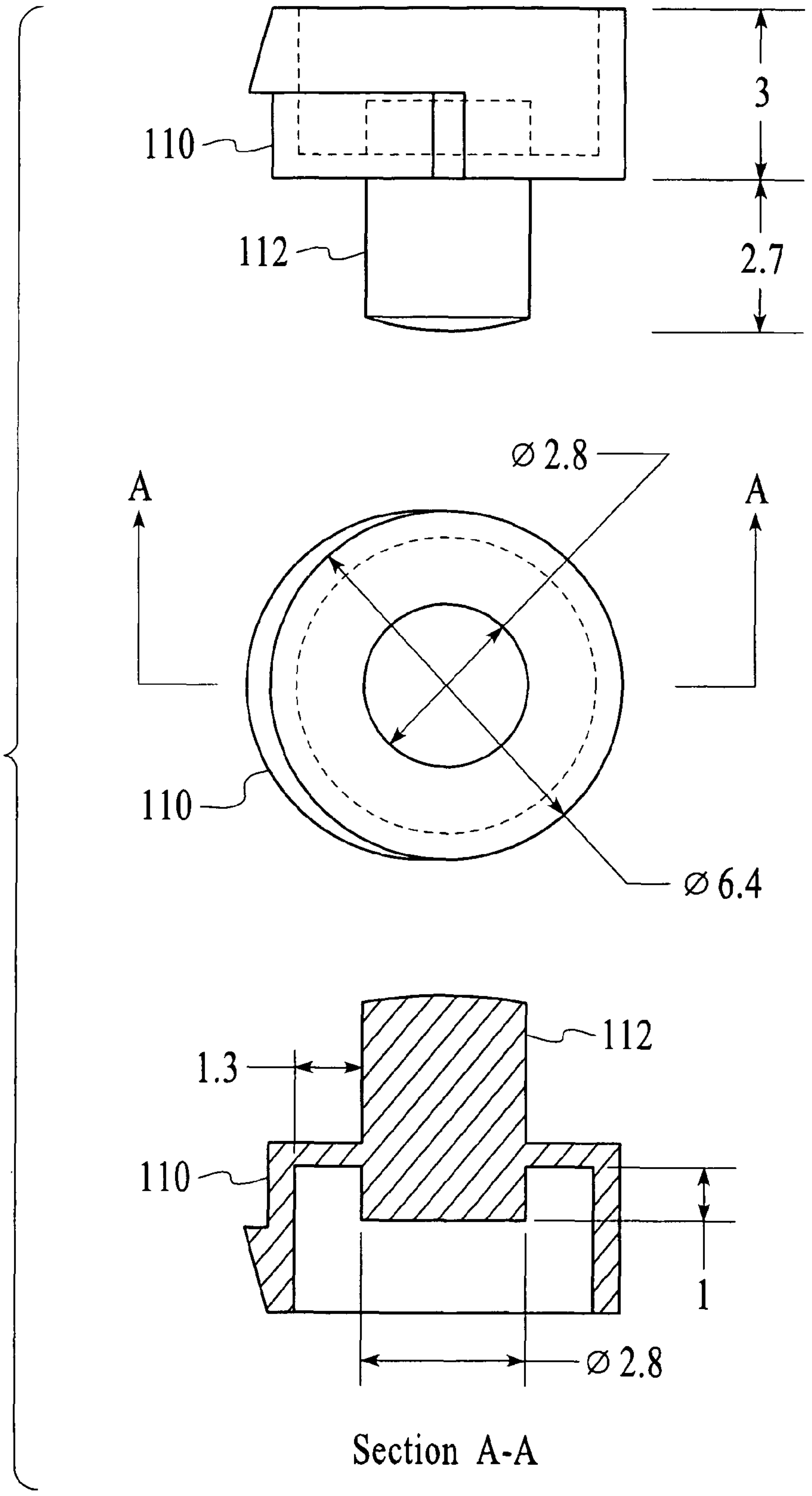
FIG.3-A
Section A-A

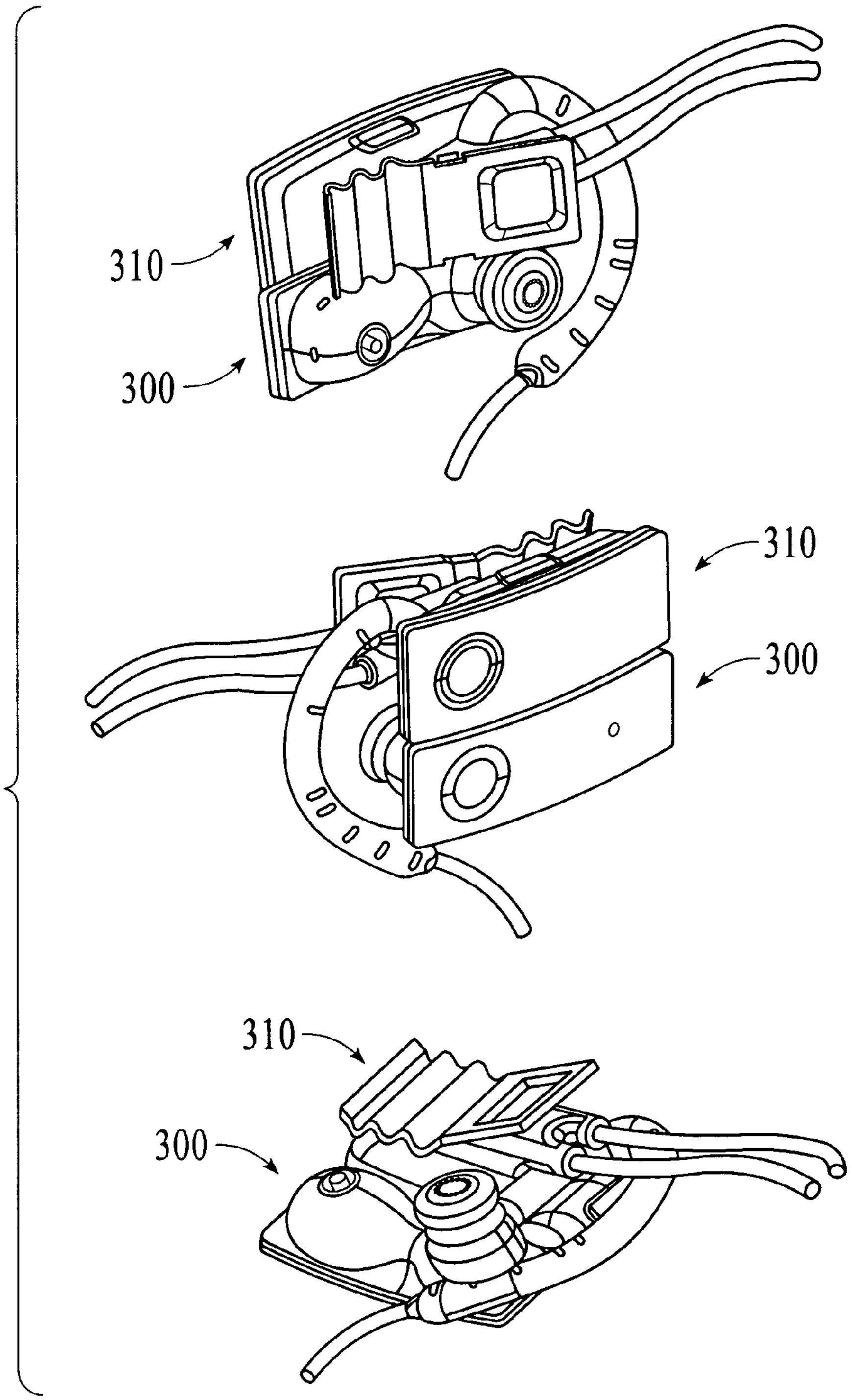
FIG.3-B

FIG.4-A
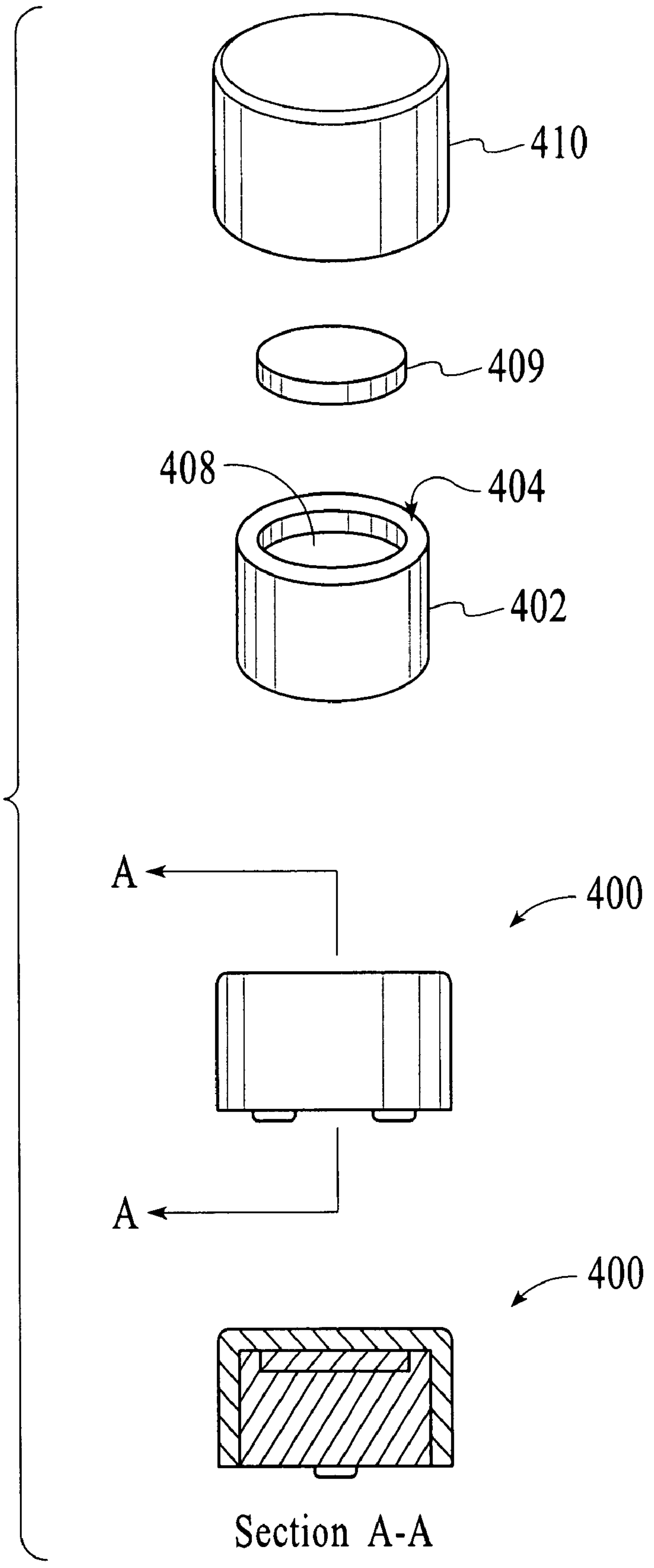
Section A-A

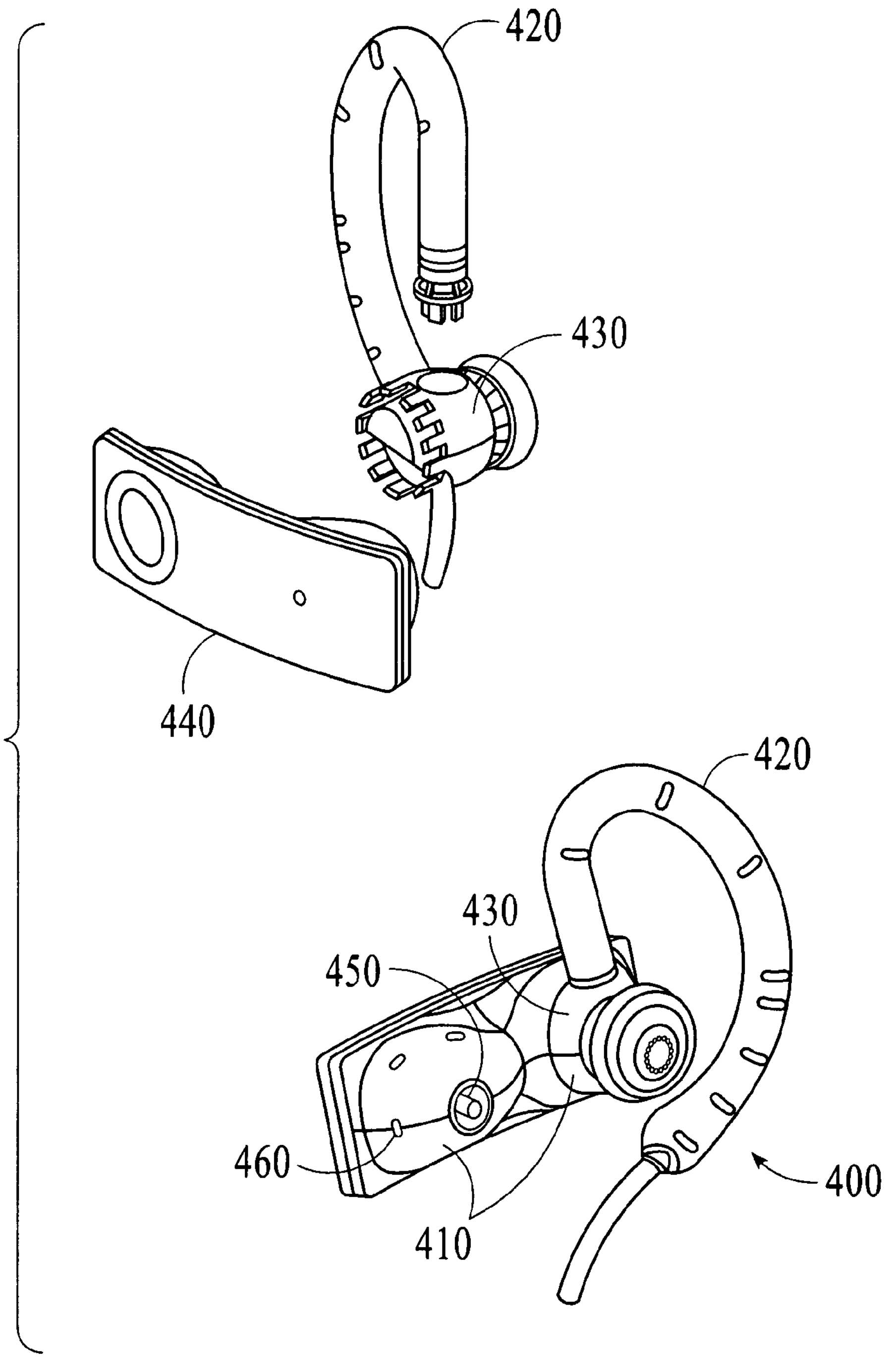
FIG.4-B

FIG.5-A
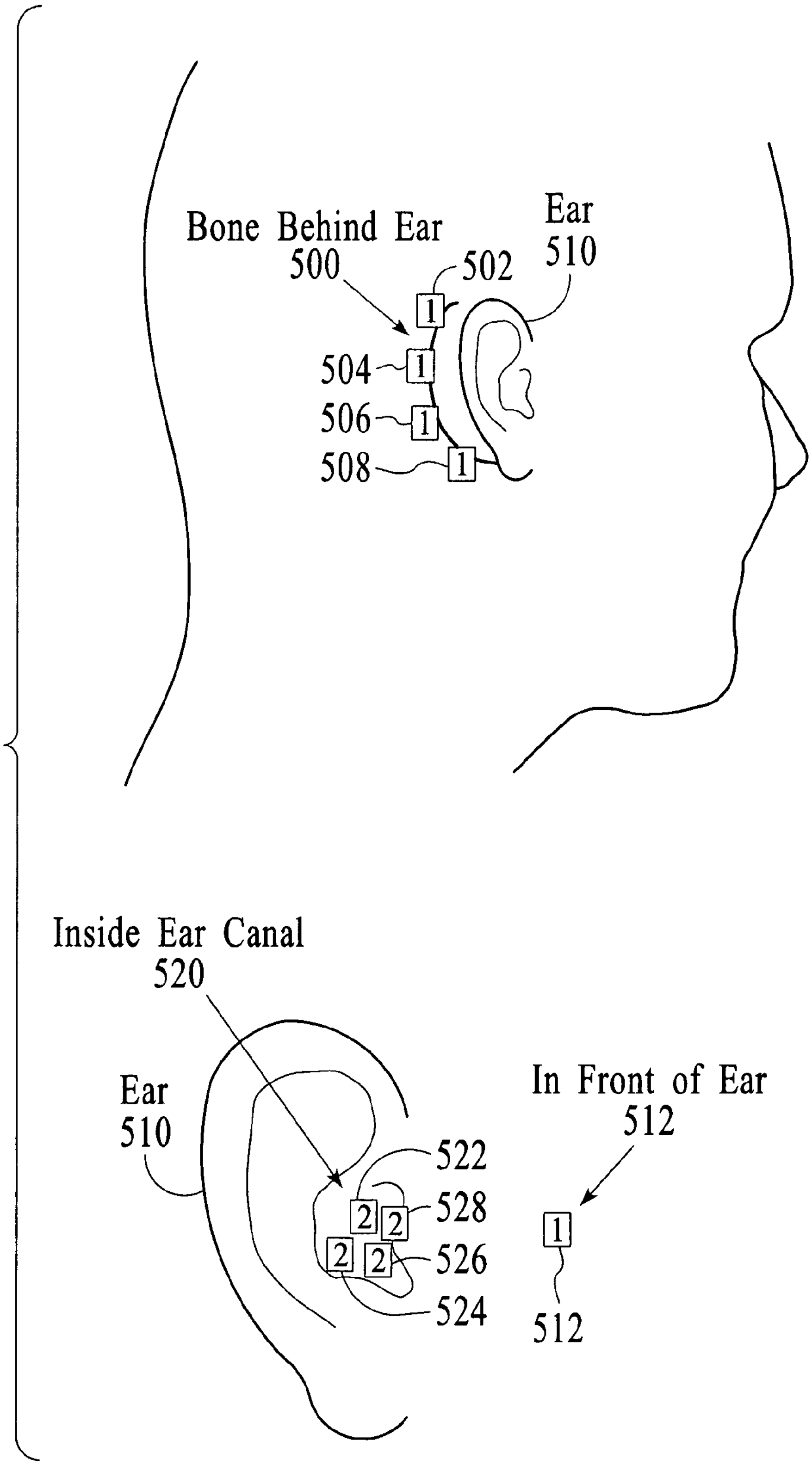

FIG.5-B

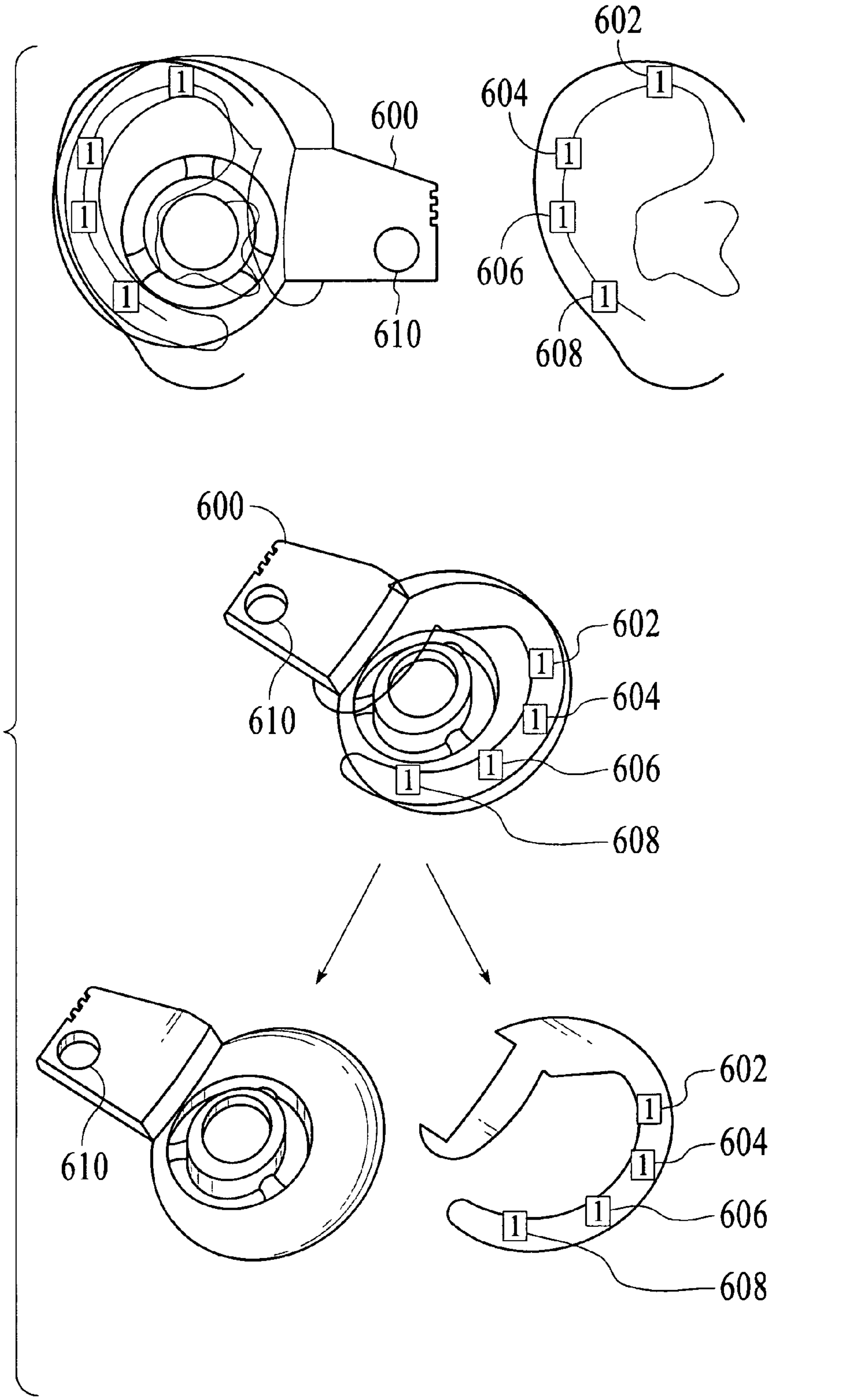
FIG.6-A

FIG.6-B
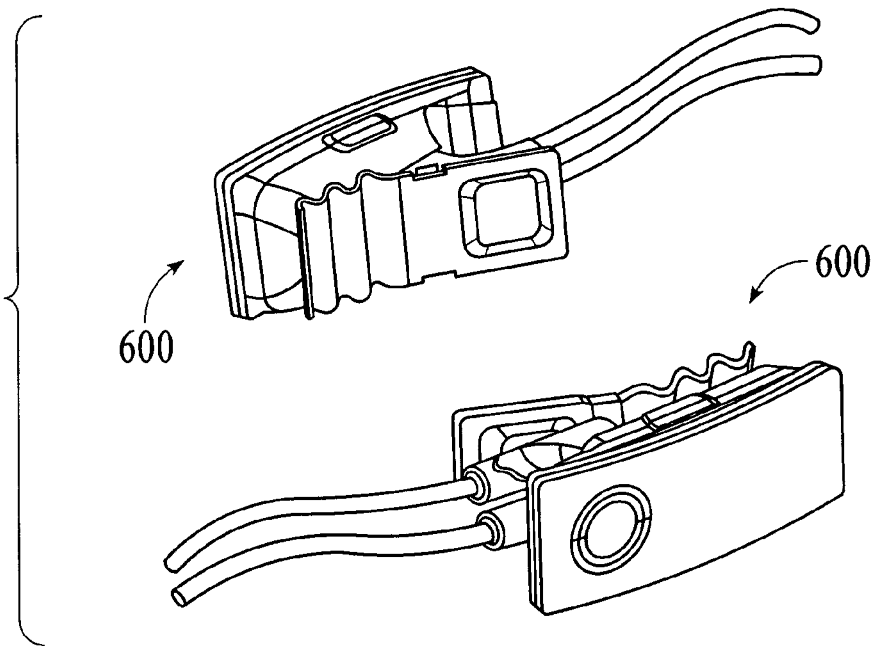
FIG.7
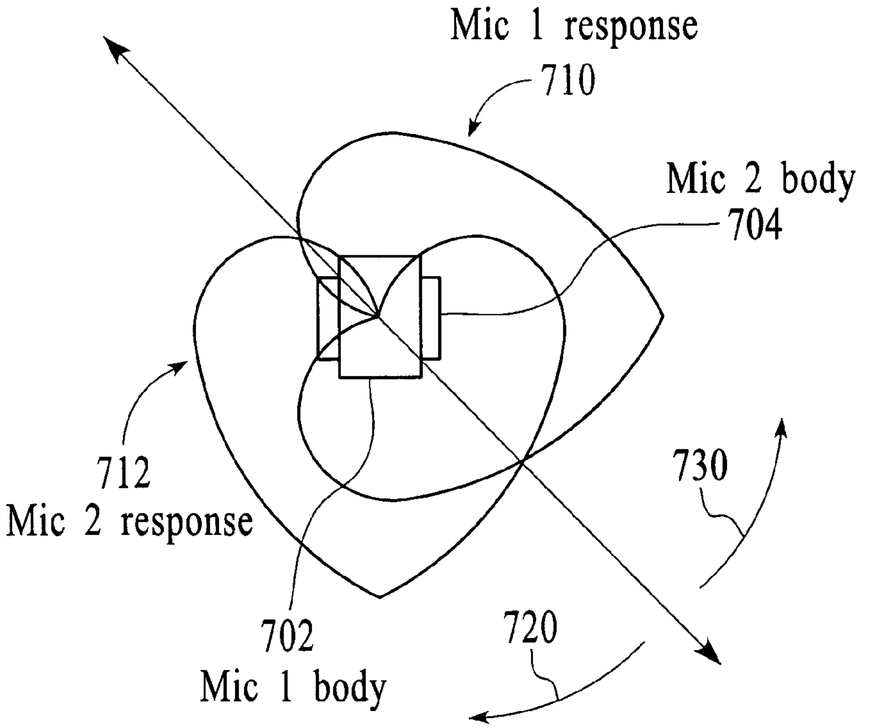

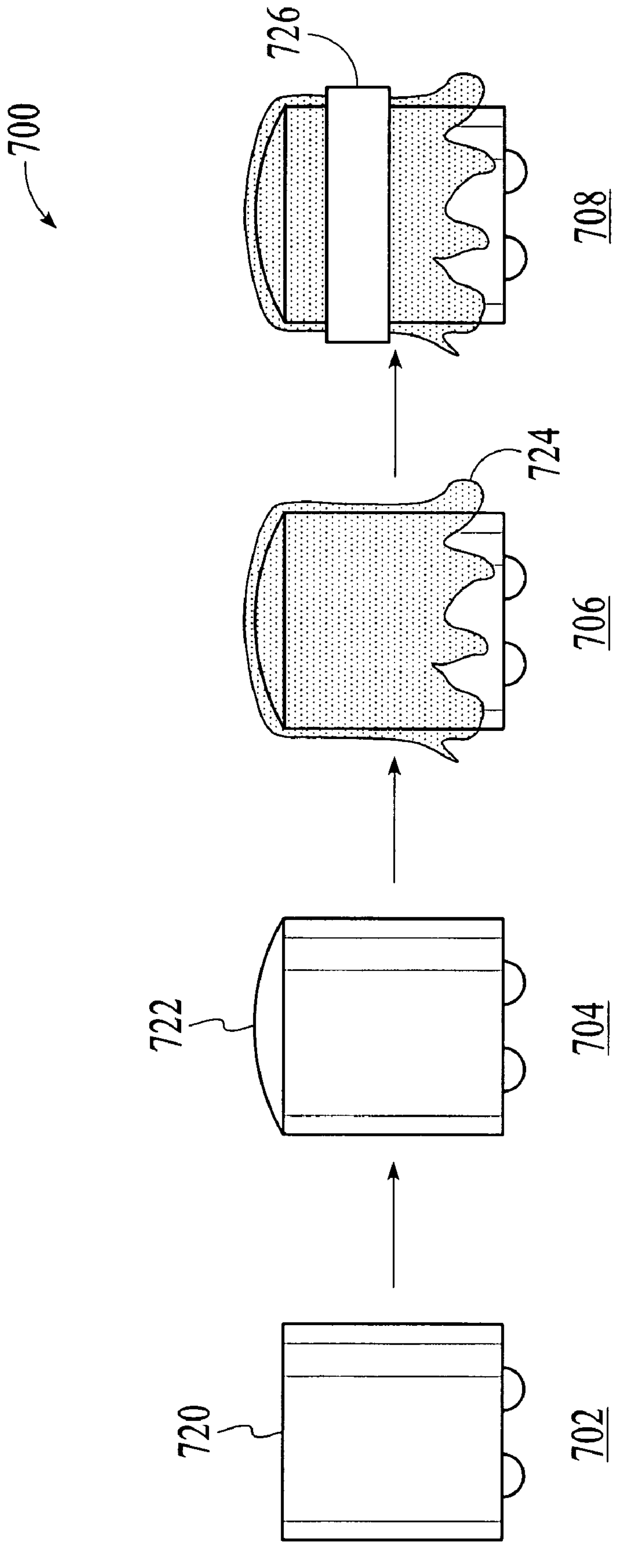
FIG.7-A

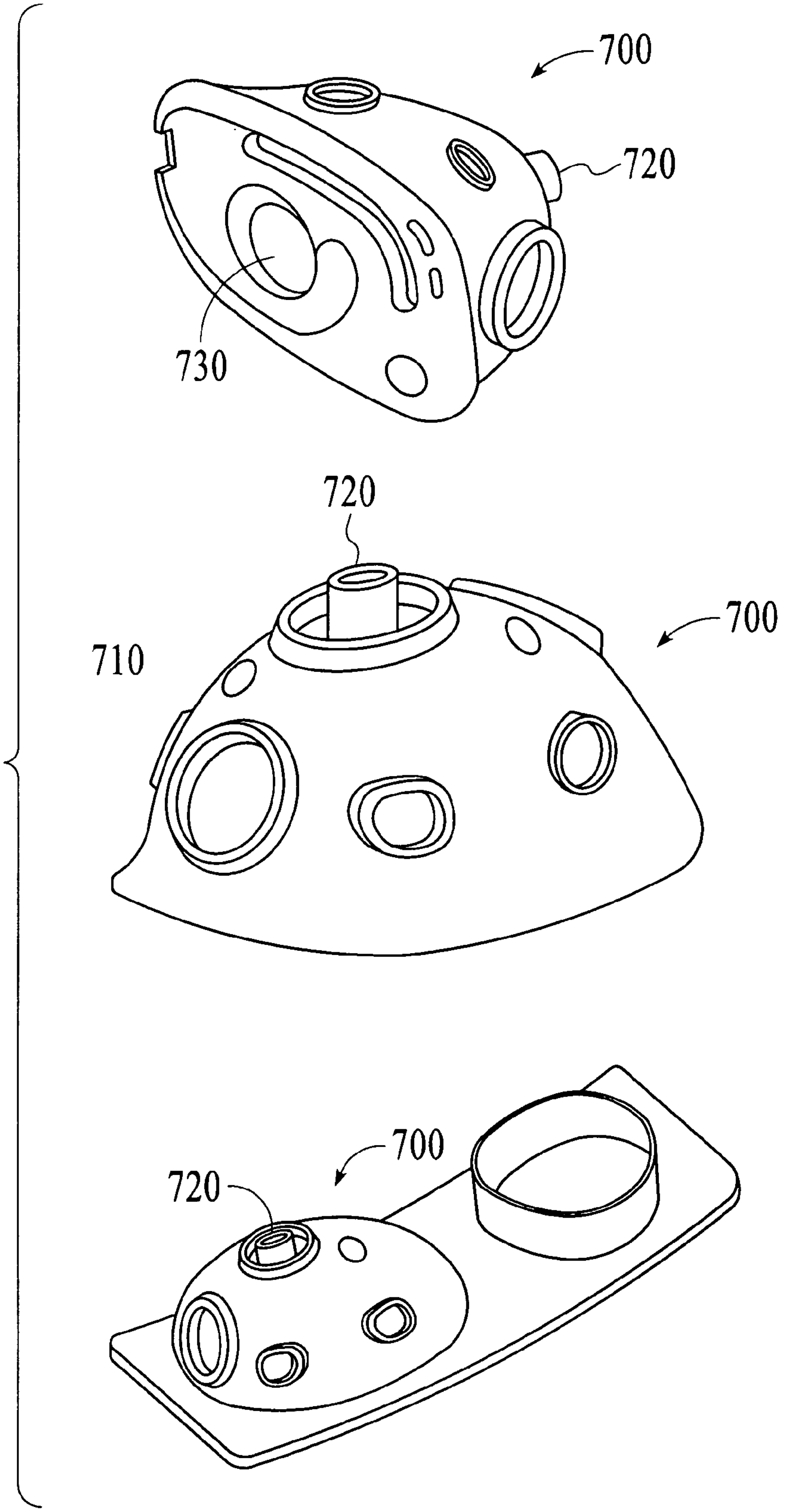
FIG.7-B

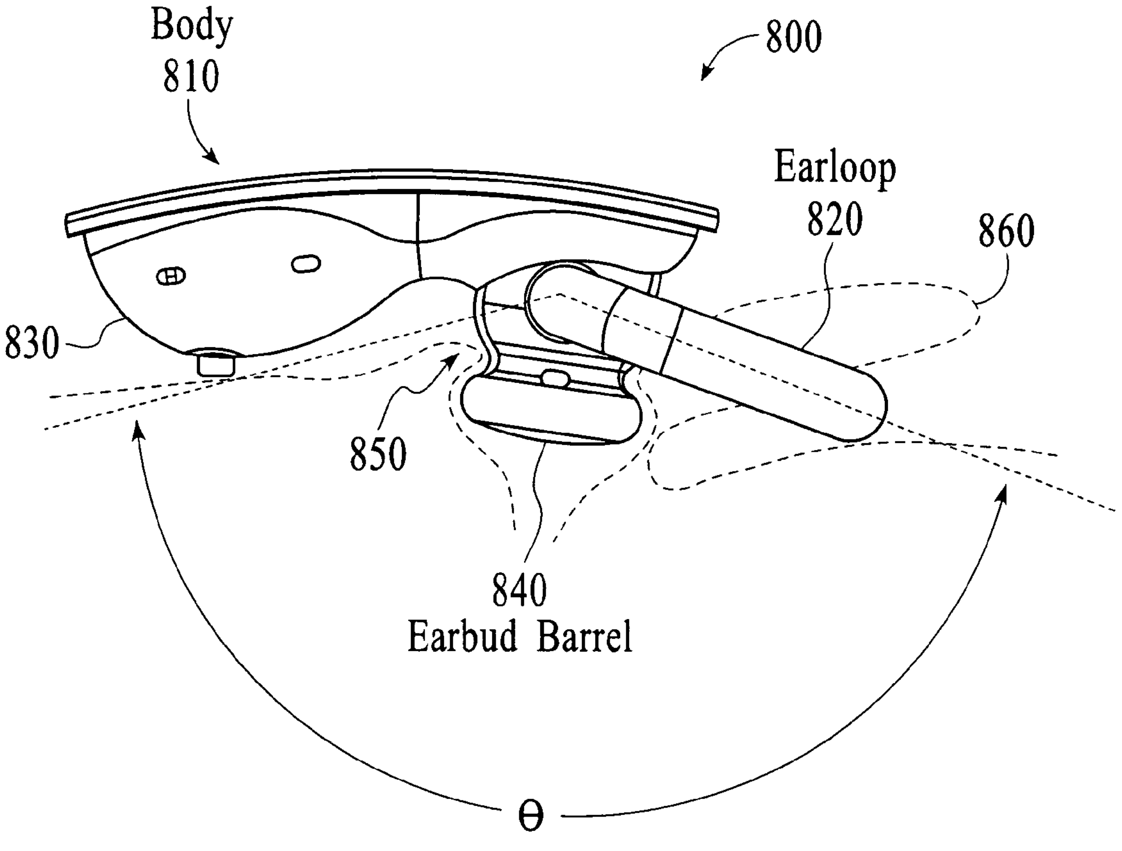
FIG.8-B

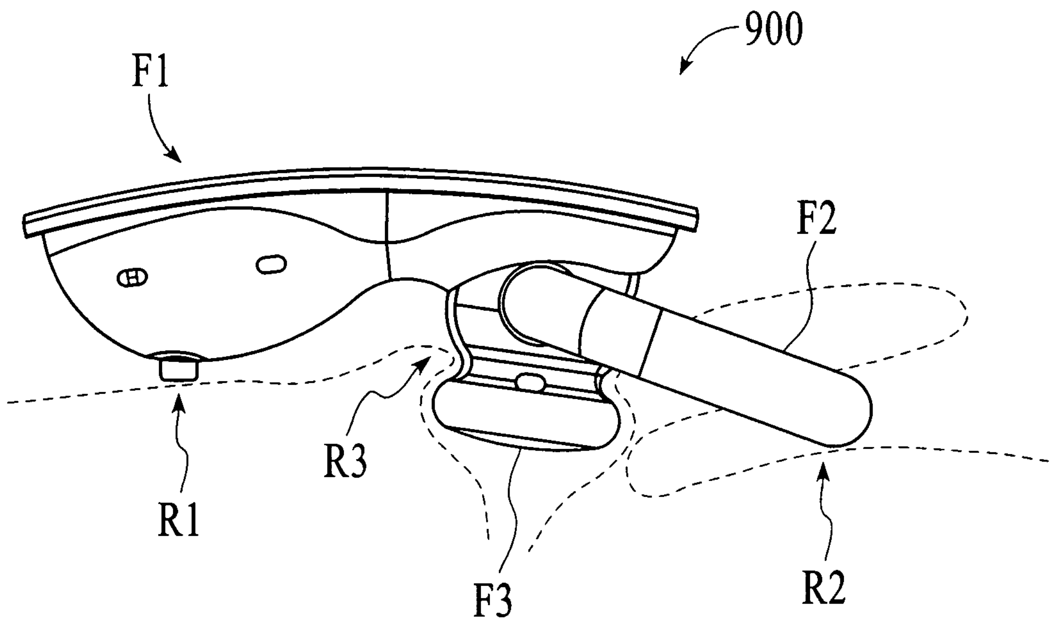
FIG.9-B
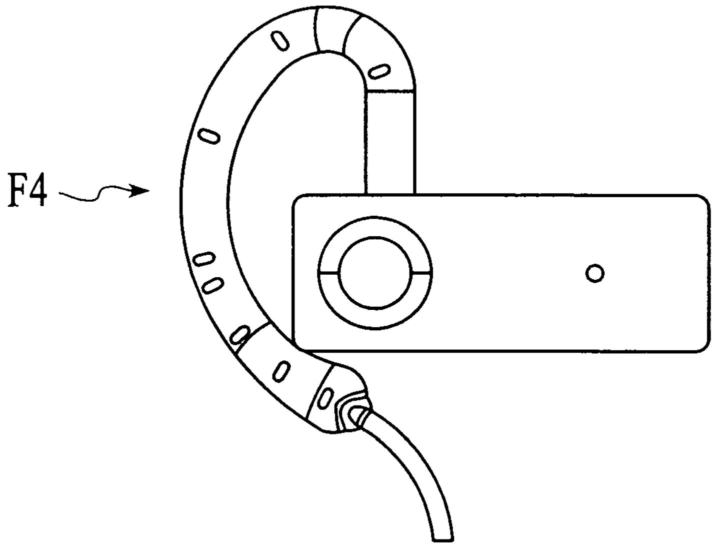
FIG.10-B

NOISE SUPPRESSING MULTI-MICROPHONE HEADSET

RELATED APPLICATIONS

This application claims the benefit of U.S. Provisional Patent Application Ser. No. 60/599,468, titled "Jawbone Headset" and filed Aug. 6, 2004, which is hereby incorporated by reference herein in its entirety. This application further claims the benefit of U.S. Provisional Patent Application Ser. No. 60/599,618, titled "Wind and Noise Compensation in a Headset" and filed Aug. 6, 2004, which is hereby incorporated by reference herein in its entirety.

This application is related to the following U.S. patent applications assigned to Aliph, of Brisbane, Calif. These include:

1. A unique noise suppression algorithm (reference Method and Apparatus for Removing Noise from Electronic Signals, filed Nov. 21, 2002, and Voice Activity Detector (VAD)—Based Multiple Microphone Acoustic Noise Suppression, filed Sep. 18, 2003)
2. A unique microphone arrangement and configuration (reference Microphone and Voice Activity Detection (VAD) Configurations for use with Communications Systems, filed Mar. 27, 2003)
3. A unique voice activity detection (VAD) sensor, algorithm, and technique (reference Acoustic Vibration Sensor, filed Jan. 30, 2004, and Voice Activity Detection (VAD) Devices and Systems, filed Nov. 20, 2003)
4. An incoming audio enhancement system named Dynamic Audio Enhancement (DAE) that filters and amplifies the incoming audio in order to make it simpler for the user to better hear the person on the other end of the conversation (i.e. the "far end").
5. A unique headset configuration that uses several new techniques to ensure proper positioning of the loudspeaker, microphones, and VAD sensor as well as a comfortable and stable position.

All of the U.S. patents referenced herein are incorporated by reference herein in their entirety.

FIELD

The disclosed embodiments relate to systems and methods for detecting and processing a desired signal in the presence of acoustic noise.

BACKGROUND

Many noise suppression algorithms and techniques have been developed over the years. Most of the noise suppression systems in use today for speech communication systems are based on a single-microphone spectral subtraction technique first develop in the 1970's and described, for example, by S. F. Boll in "Suppression of Acoustic Noise in Speech using Spectral Subtraction," IEEE Trans. on ASSP, pp. 113-120, 1979. These techniques have been refined over the years, but the basic principles of operation have remained the same. See, for example, U.S. Pat. No. 5,687,243 of McLaughlin, et al., and U.S. Pat. No. 4,811,404 of Vilmur, et al. Generally, these techniques make use of a microphone-based Voice Activity Detector (VAD) to determine the background noise characteristics, where "voice" is generally understood to include human voiced speech, unvoiced speech, or a combination of voiced and unvoiced speech.

The VAD has also been used in digital cellular systems. As an example of such a use, see U.S. Pat. No. 6,453,291 of Ashley, where a VAD configuration appropriate to the frontend of a digital cellular system is described. Further, some Code Division Multiple Access (CDMA) systems utilize a VAD to minimize the effective radio spectrum used, thereby allowing for more system capacity. Also, Global System for Mobile Communication (GSM) systems can include a VAD to reduce co-channel interference and to reduce battery consumption on the client or subscriber device.

These typical microphone-based VAD systems are significantly limited in capability as a result of the addition of environmental acoustic noise to the desired speech signal received by the single microphone, wherein the analysis is performed using typical signal processing techniques. In particular, limitations in performance of these microphone-based VAD systems are noted when processing signals having a low signal-to-noise ratio (SNR), and in settings where the background noise varies quickly. Thus, similar limitations are found in noise suppression systems using these microphone-based VADs.

BRIEF DESCRIPTION OF THE FIGURES

FIG. 7: Simulated magnitude responses for Mic1 and Mic2 of Jawbone-type microphone configuration at a single frequency.

FIG. 1-A: Side slice view of an SSM (acoustic vibration sensor).

FIG. 2A-A: Exploded view of an SSM.

FIG. 2B-A: Perspective view of an SSM.

FIG. 3-A: Schematic diagram of an SSM coupler.

FIG. 4-A: Exploded view of an SSM under an alternative embodiment.

FIG. 5-A: Representative areas of SSM sensitivity on the human head.

FIG. 6-A: Generic headset with SSM placed at many different locations.

FIG. 7-A: Diagram of a manufacturing method that may be used to construct an SSM.

FIG. 1-B: Perspective view of an assembled Jawbone earpiece.

FIG. 2-B: Perspective view of other side of Jawbone earpiece.

FIG. 3-B: Perspective view of assembled Jawbone earpiece.

FIG. 4-B: Perspective Exploded and Assembled view of Jawbone earpiece.

FIG. 5-B: Perspective exploded view of torsional spring-loading mechanism of Jawbone earpiece.

FIG. 6-B: Perspective view of control module.

FIG. 7-B: Perspective view of microphone and sensor booty of Jawbone earpiece.

FIG. 8-B: Top view orthographic drawing of headset on ear illustrating the angle between the earloop and body of Jawbone earpiece.

FIG. 9-B: Top view orthographic drawing of headset on ear illustrating forces on earpiece and head of user.

FIG. 10-B: Side view orthographic drawing of headset on ear illustrating force applied by earpiece to pinna.

DETAILED DESCRIPTION

The Pathfinder Noise Suppression System

Figure 1:
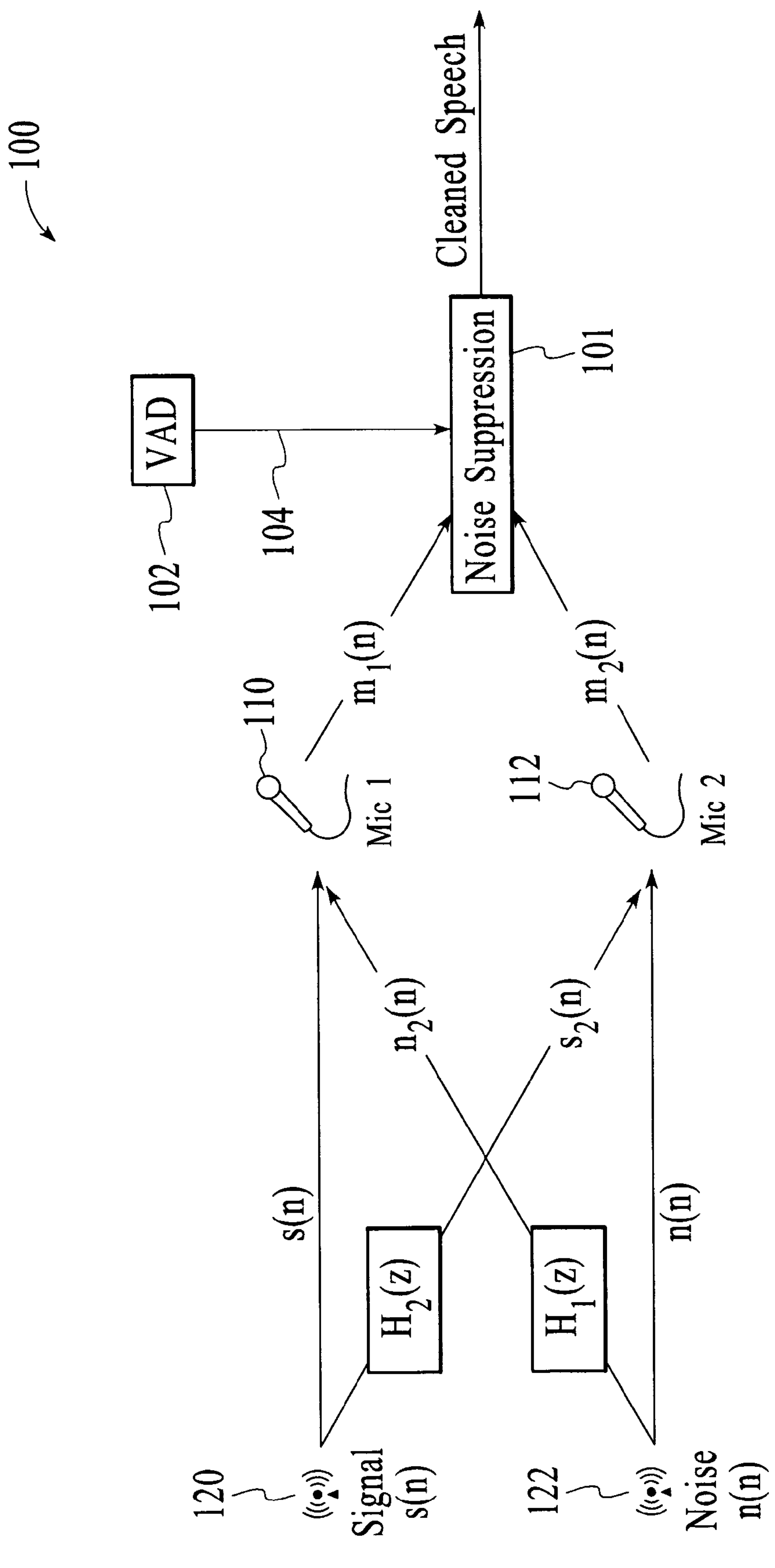
FIG. 1: Overview of the Pathfinder noise suppression system.

FIG. 1 is a block diagram of the Pathfinder noise suppression system 100 including the Pathfinder noise suppression algorithm 101 and a VAD system 102, under an embodiment. It also includes two microphones MIC 1 110 and MIC 2 112 that receive signals or information from at least one speech source 120 and at least one noise source 122. The path s(n) from the speech source 120 to MIC 1 and the path n(n) from the noise source 122 to MIC 2 are considered to be unity. Further, $H_1(z)$ represents the path from the noise source 122 to MIC 1, and $H_2(z)$ represents the path from the signal source 120 to MIC 2.

Figure 2:
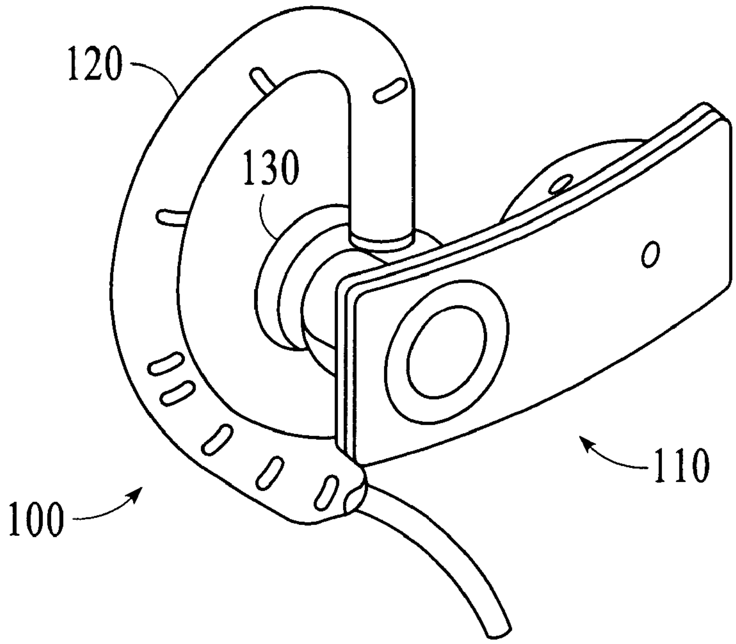
FIG. 2: Overview of the VAD device relationship with the VAD algorithm and the noise suppression algorithm.
Figure 2:
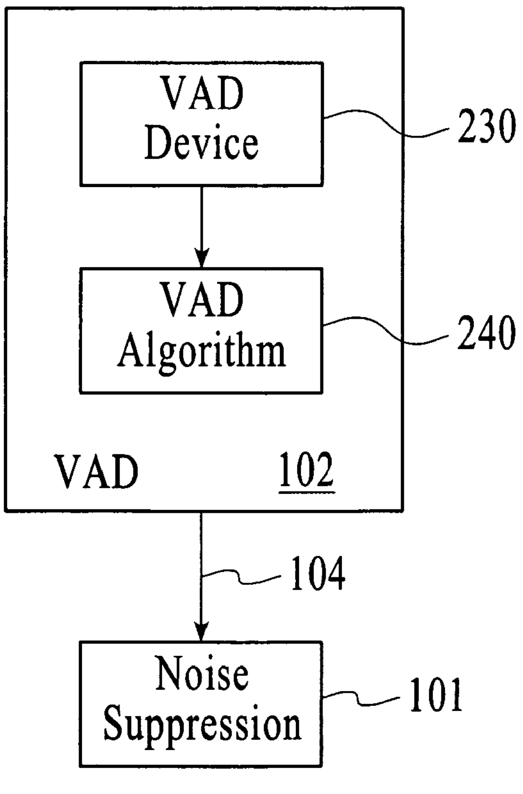
Figure 3:
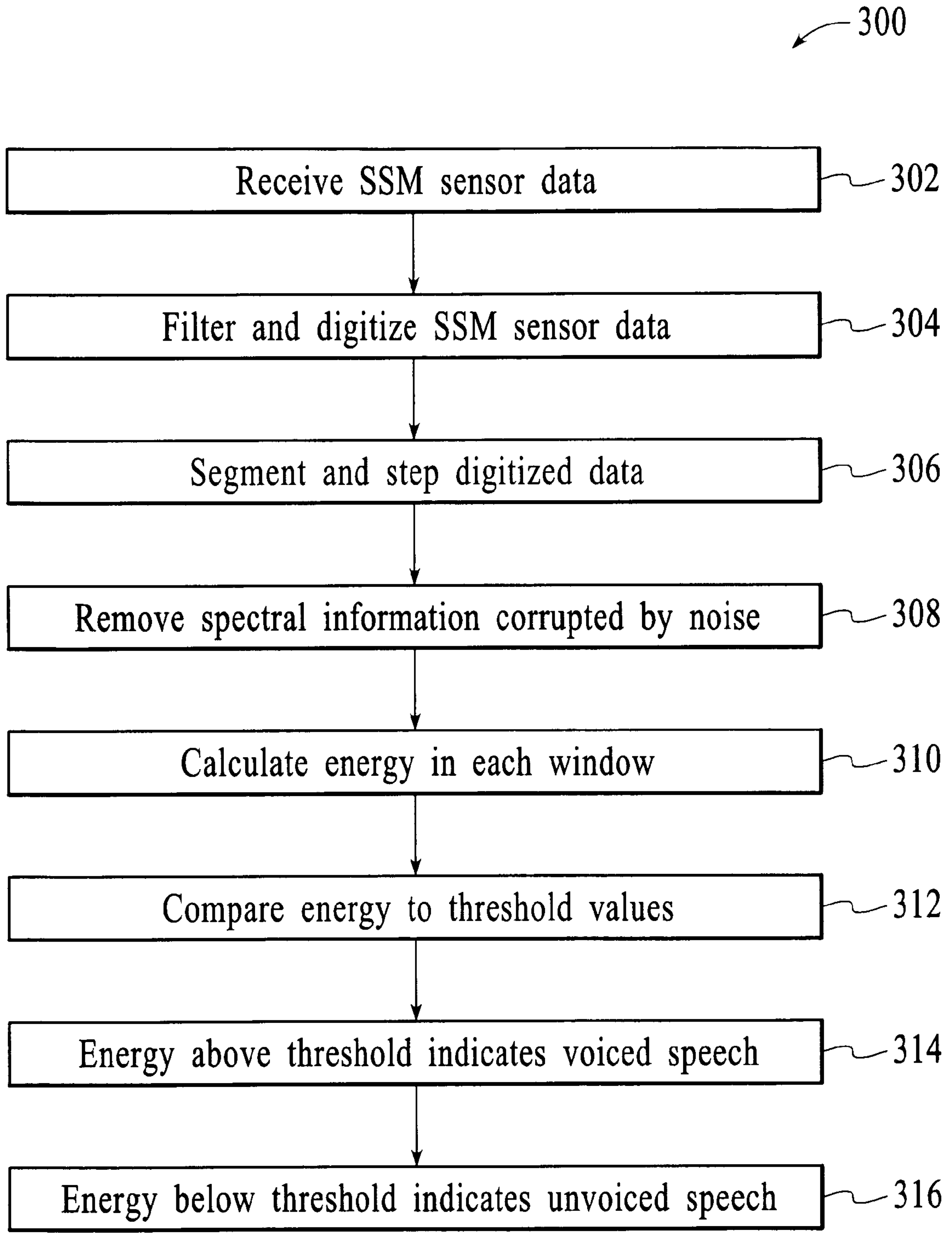
FIG. 3: Flow chart of SSM sensor VAD embodiment.

A VAD signal 104, derived in some manner, is used to control the method of noise removal, and is related to the noise suppression technique discussed below as shown in FIG. 2. A preview of the VAD technique discussed below using an acoustic transducer (called the Skin Surface Microphone, or SSM) is shown in FIG. 3. Referring back to FIG. 1, the acoustic information coming into MIC 1 is denoted by $m_1(n)$. The information coming into MIC 2 is similarly labeled $m_2(n)$. In the z (digital frequency) domain, we can represent them as $M_1(z)$ and $M_2(z)$. Thus $$M_1(z)=S(z)+N(z)H_1(z)$$

$$M_2(z)=N(z)+S(z)H_2(z) \quad (1)$$

This is the general case for all realistic two-microphone systems. There is always some leakage of noise into MIC 1, and some leakage of signal into MIC 2. Equation 1 has four unknowns and only two relationships and, therefore, cannot be solved explicitly. However, perhaps there is some way to solve for some of the unknowns in Equation 1 by other means. Examine the case where the signal is not being generated, that is, where the VAD indicates voicing is not occurring. In this case, s(n)=S(z)=0, and Equation 1 reduces to $$M_{1n}(z)=N(z)H_1(z)$$

$$M_{2n}(z)=N(z)$$

where the n subscript on the M variables indicate that only noise is being received. This leads to $$M_{1n}(z) = M_{2n}(z)H_1(z) \quad (2)$$

$$H_1(z) = \frac{M_{1n}(z)}{M_{2n}(z)}.$$

Now, $H_1(z)$ can be calculated using any of the available system identification algorithms and the microphone outputs when only noise is being received. The calculation should be done adaptively in order to allow the system to track any changes in the noise.

After solving for one of the unknowns in Equation 1, $H_2(z)$ can be solved for by using the VAD to determine when voicing is occurring with little noise. When the VAD indicates voicing, but the recent (on the order of 1 second or so) history of the microphones indicate low levels of noise, assume that n(s)=N(z)~0. Then Equation 1 reduces to $$M_{1s}(z)=S(z)$$

$$M_{2s}(z)=S(z)H_2(z)$$

which in turn leads to $$M_{2s}(z) = M_{1s}(z)H_2(z)$$

$$H_2(z) = \frac{M_{2s}(z)}{M_{1s}(z)}$$

This calculation for $H_2(z)$ appears to be just the inverse of the $H_1(z)$ calculation, but remember that different inputs are being used. Note that $H_2(z)$ should be relatively constant, as there is always just a single source (the user) and the relative position between the user and the microphones should be relatively constant. Use of a small adaptive gain for the $H_2(z)$ calculation works well and makes the calculation more robust in the presence of noise.

Following the calculation of $H_1(z)$ and $H_2(z)$ above, they are used to remove the noise from the signal. Rewriting Equation 1 as $$S(z)=M_1(z)-N(z)H_1(z)$$

$$N(z)=M_2(z)-S(z)H_2(z)$$

$$S(z)=M_1(z)-[M_2(z)-S(z)H_2(z)]H_1(z)$$

$$S(z)[1-H_2(z)H_1(z)]=M_1(z)-M_2(z)H_1(z)$$

allows solving for S(z)

$$S(z) = \frac{M_1(z) - M_2(z)H_1(z)}{1 - H_2(z)H_1(z)}. \quad (3)$$

Generally, $H_2(z)$ is quite small, and $H_1(z)$ is less than unity, so for most situations at most frequencies $$H_2(z)H_1(z) \ll 1,$$

and the signal can be estimated using $$S(z) \approx M_1(z)-M_2(z)H_1(z) \quad (4)$$

Therefore the assumption is made that $H_2(z)$ is not needed, and $H_1(z)$ is the only transfer function to be calculated. While $H_2(z)$ can be calculated if desired, good microphone placement and orientation can obviate the need for the $H_2(z)$ calculation.

Significant noise suppression can best be achieved through the use of multiple subbands in the processing of acoustic signals. This is because most adaptive filters used to calculate transfer functions are of the FIR type, which use only zeros and not poles to calculate a system that contains both zeros and poles as $$H_1(z) \xrightarrow[MODELS]{} \frac{B(z)}{A(z)}.$$

Such a model can be sufficiently accurate given enough taps, but this can greatly increases computational cost and convergence time. What generally occurs in an energy-based adaptive filter system such as the least-mean squares (LMS) system is that the system matches the magnitude and phase well at a small range of frequencies that contain more energy than other frequencies. This allows the LMS to fulfill its requirement to minimize the energy of the error to the best of its ability, but this fit may cause the noise in areas outside of the matching frequencies to rise, reducing the effectiveness of the noise suppression.

The use of subbands alleviates this problem. The signals from both the primary and secondary microphones are filtered into multiple subbands, and the resulting data from each subband (which can be frequency shifted and decimated if desired, but it is not necessary) is sent to its own adaptive filter. This forces the adaptive filter to try to fit the data in its own subband, rather than just where the energy is highest in the signal. The noise-suppressed results from each subband can be added together to form the final denoised signal at the end. Keeping everything time-aligned and compensating for filter shifts is essential, and the result is a much better model to the system than the single-subband model at the cost of increased memory and processing requirements.

Figure 4:
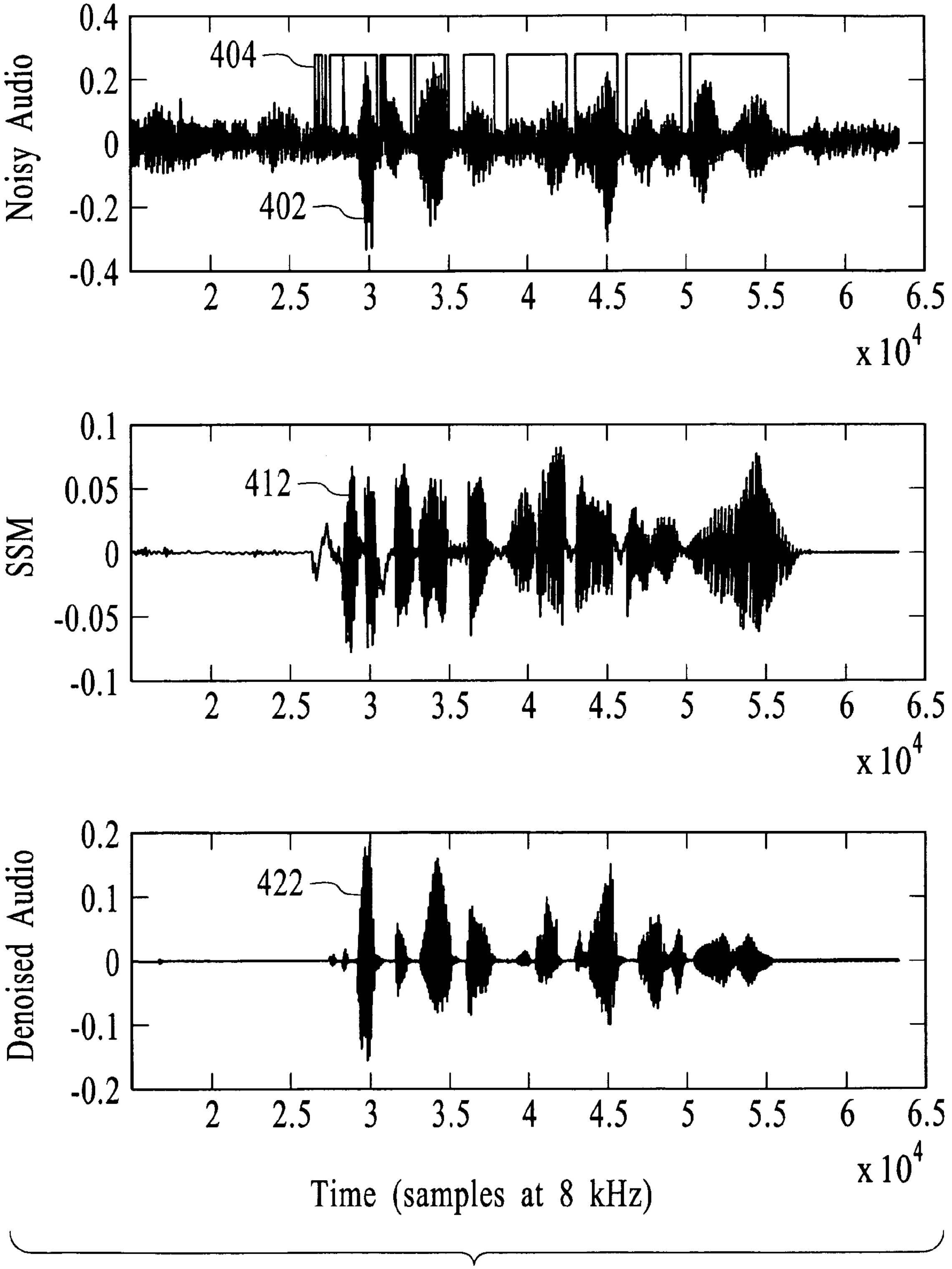
FIG. 4: Example of noise suppression performance using the SSM VAD.

An example of the noise suppression performance using this system with an SSM VAD device is shown in FIG. 4. In the top plot is the original noisy acoustic signal 402 and the SSM-derived VAD signal 404, the middle plot displays the SSM signal as taken on the cheek 412, and the bottom plot the cleaned signal after noise suppression 422 using the Pathfinder algorithm outline above.

More information may be found in the applications referenced above in the Introduction, part 1.

Microphone Configuration

In an embodiment of the Pathfinder noise suppression system, unidirectional or omnidirectional microphones may be employed. A variety of microphone configurations that enable Pathfinder are shown in the references in the Introduction, part 2. We will examine only a single embodiment as implemented in the Jawbone headset, but many implementations are possible as described in the references cited in the Introduction, so we are not so limited by this embodiment.

The use of directional microphones has been very successful and is used to ensure that the transfer functions $H_1(z)$ and $H_2(z)$ remain significantly different. If they are too similar, the desired speech of the user can be significantly distorted. Even when they are dissimilar, some speech signal is received by the noise microphone. If it is assumed that $H_2(z)=0$, then, as in Equation 4 above, even assuming a perfect VAD there will be some distortion. This can be seen by referring to Equation 3 and solving for the result when $H_2(z)$ is not included:

$$S(z)[1-H_2(z)H_1(z)]=M_1(z)-M_2(z)H_1(z). \quad (5)$$

This shows that the signal will be distorted by the factor $[1-H_2(z)H_1(z)]$. Therefore, the type and amount of distortion will change depending on the noise environment. With very little noise, $H_1(z)$ is nearly zero and there is very little distortion. With noise present, the amount of distortion may change with the type, location, and intensity of the noise source(s). Good microphone configuration design minimizes these distortions.

Figure 5:
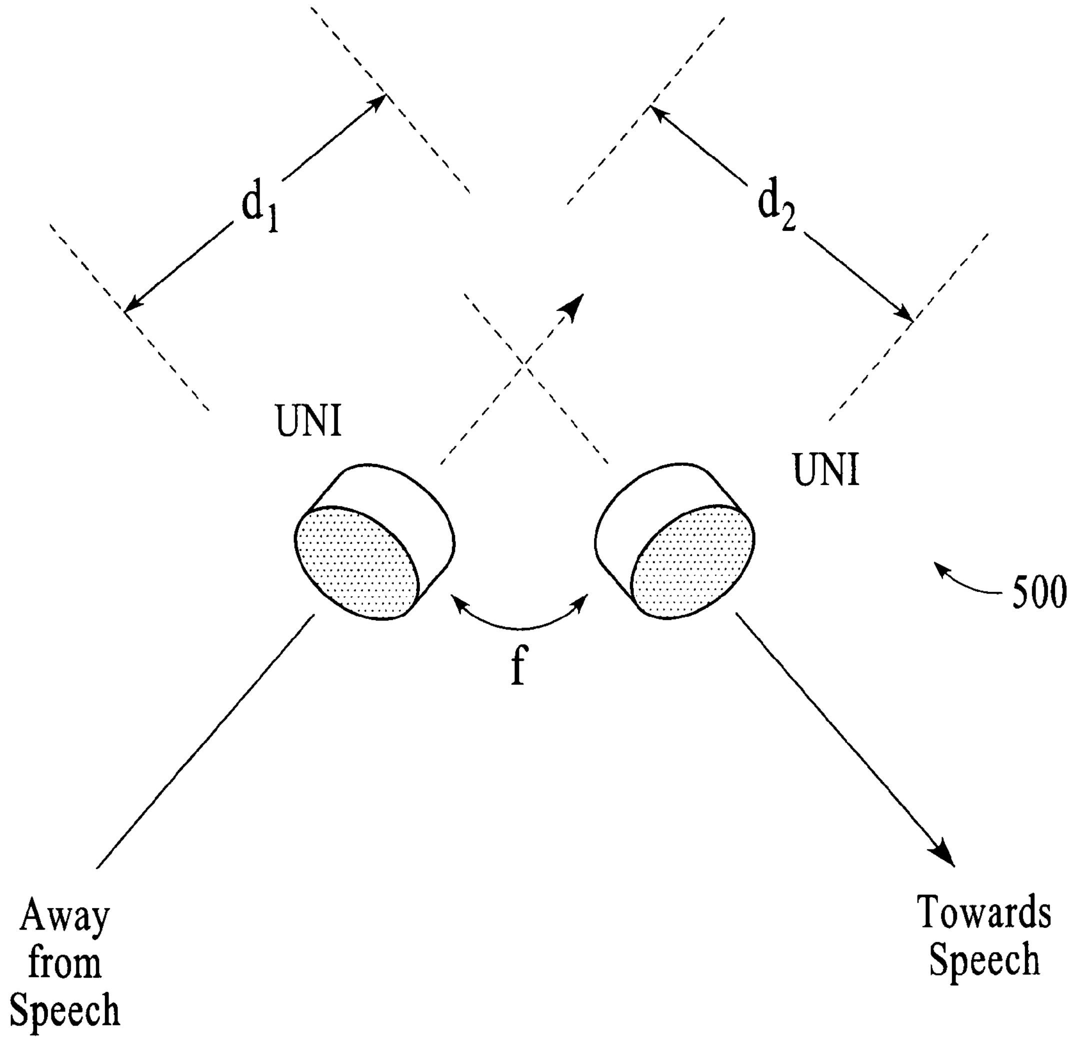
FIG. 5: A specific microphone configuration embodiment as used with the Jawbone headset.
Figure 6:
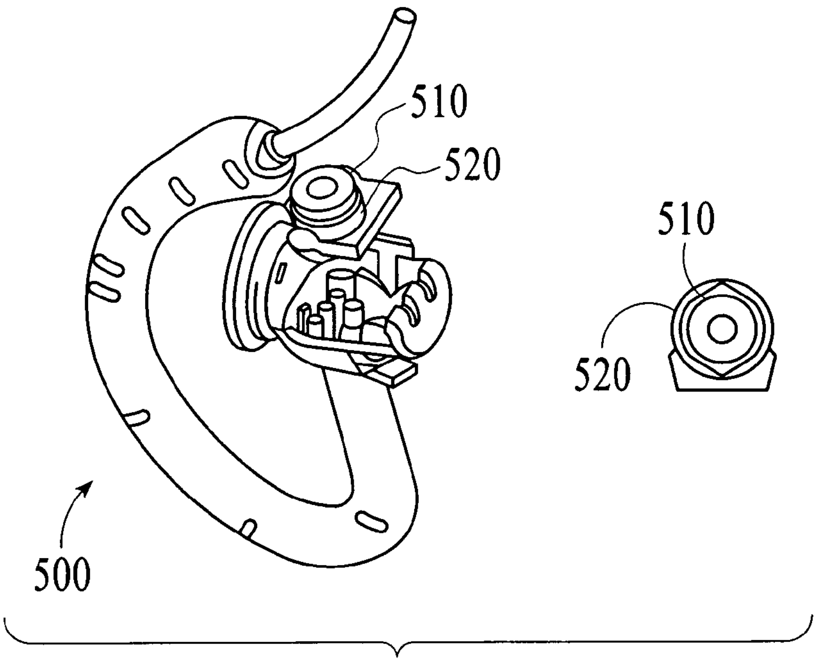
FIG. 6: Simulated magnitude response of a cardioid microphone at a single frequency.
Figure 6:
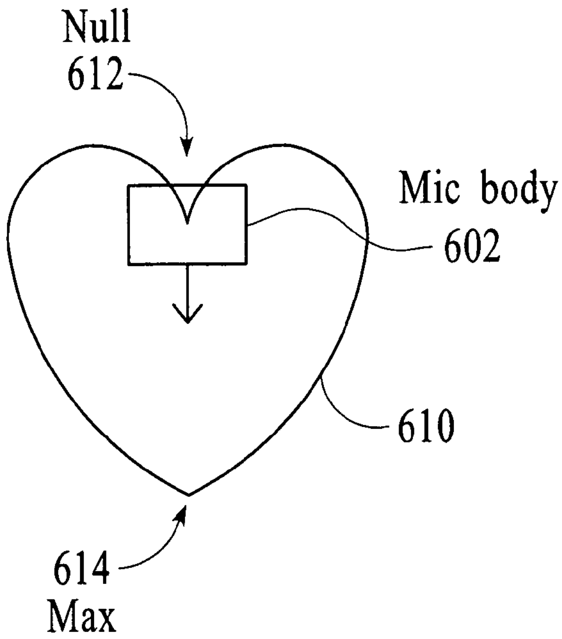

An embodiment of an appropriate microphone configuration is one in which two directional microphones are used as shown in configuration 500 in FIG. 5. The relative angle f between vectors normal to the faces of the microphones is in a range between 60 and 135 degrees. The distances $d_1$ and $d_2$ are each in the range of zero (0) to 15 centimeters, with best performance coming with distances between 0 and 2 cm. This configuration orients one the speech microphone, termed MIC1 above, toward the user's mouth, and the noise microphone, termed MIC2 above, away from the user's mouth. Assuming that the two microphones are identical in terms of spatial and frequency response, changing the value of the angle f will change the overlap of the responses of the microphones. This is demonstrated in FIG. 6 and FIG. 7 for cardioid microphones. In FIG. 6, a simulated spatial response at a single frequency is shown for a cardioid microphone. The body of the microphone is denoted by 602, the response by 610, the null of the response by 612, and the maximum of the response by 614. In FIG. 7, the responses of two cardioid microphones are shown with f=90 degrees. The responses overlap, and where the response of Mic1 is greater than that of Mic2 the gain G $$G = \left|\frac{M_1(z)}{M_2(z)}\right|$$

is greater than 1 (730), and where the response of Mic1 is less than Mic2 G is less than 1 (720). Clearly as the angle f between the microphones is varied, the amount of overlap and thus the areas where G is greater or less than one varies as well. This variation affects the noise suppression performance both in terms of the amount of noise suppression and the amount of speech distortion, and a good compromise between the two must be found by adjusting f until satisfactory performance is realized.

In addition, the overlap of microphone responses can be induced or further changed by the addition of front and rear vents to the microphone mount. These vents change the response of the microphone by altering the delay between the front and rear faces of the diaphragm. Thus, vents can be used to alter the response overlap and thereby change the denoising performance of the system.

Design Tips:

A good microphone configuration can be difficult to construct. The foundation of the process is to use two microphones that have similar noise fields and different speech fields. Simply put, to the microphones the noise should appear to be about the same and the speech should be different. This similarity for noise and difference for speech allows the algorithm to remove noise efficiently and remove speech poorly, which is desired. Proximity effects can be used to further increase the noise/speech difference (NSD) when the microphones are located close to the mouth, but orientation is the primary difference vehicle when the microphones are more than about five to ten centimeters from the mouth. The NSD is defined as the amount of difference in the speech energy detected by the microphones minus the difference in the noise energy in dB. NSDs of 4-6 dB result in both good noise suppression and low speech distortion. NSDs of 0-4 dB result in excellent noise suppression but high speech distortion, and NSDs of 6+ dB result in good to poor noise suppression and very low speech distortion. Naturally, since the response of a directional microphone is directly related to frequency, the NSD will also be frequency dependent, and different frequencies of the same noise or speech may be denoised or devoiced by different amounts depending on the NSD for that frequency.

Another very important stipulation is that there should be little or no noise in Mic1 that is not detected in some way by Mic2. In fact, generally, the closer the levels (energies) of the noise in Mic1 and Mic2, the better the noise suppression. However, if the speech levels are about the same in both microphones, then speech distortion due to de-voicing will also be high, and the overall increase in SNR may be low. Therefore it is crucial that the noise levels be as similar as possible while the speech levels are as different as possible. It is normally not possible to simultaneously minimize noise differences while maximizing speech differences, so a compromise must be made. Experimentation with a configuration can often yield one that works reasonably well for noise suppression and acceptable speech distortion.

In summary, the design process rules can be stated as follows:

1. The noise energy should be about the same in both microphones
2. The speech energy has to be different in the microphones
3. Take advantage of proximity effect to maximize NSD
4. Keep the distance between the microphones as small as practical
5. Use venting effects on the directionality of the microphones to get the NSD to around 4-6 dB In the configuration above, the amount of response overlap, and therefore the angle between the axes of the microphones f, will depend on the responses of the microphones as well as mounting and venting of the microphones. However, a useable configuration is readily found through experimentation.

The microphone configuration implementation described above is a specific implementation of one of many possible implementations, but the scope of this application is not so limited. There are many ways to specifically implement the ideas and techniques presented above, and the specified implementation is simply one of many that are possible. For example, the references cited in the Introduction contain many different variations on the configuration of the microphones.

VAD Device

The VAD device for the Jawbone headset is based upon the references given in the Introduction part 3. It is an acoustic vibration sensor, also referred to as a speech sensing device, also referred to as a Skin Surface Microphone (SSM), and is described below. The acoustic vibration sensor is similar to a microphone in that it captures speech information from the head area of a human talker or talker in noisy environments. However, it is different than a conventional microphone in that it is designed to be more sensitive to speech frequencies detected on the skin of the user than environmental acoustic noise. This technique is normally only successful for a limited range of frequencies (normally ~100 Hz to 1000 Hz, depending on the noise level), but this is normally sufficient for excellent VAD performance.

Previous solutions to this problem have either been vulnerable to noise, physically too large for certain applications, or cost prohibitive. In contrast, the acoustic vibration sensor described herein accurately detects and captures speech vibrations in the presence of substantial airborne acoustic noise, yet within a smaller and cheaper physical package. The noise-immune speech information provided by the acoustic vibration sensor can subsequently be used in downstream speech processing applications (speech enhancement and noise suppression, speech encoding, speech recognition, talker verification, etc.) to improve the performance of those applications.

The following description provides specific details for a thorough understanding of, and enabling description for, embodiments of a transducer. However, one skilled in the art will understand that the invention may be practiced without these details. In other instances, well-known structures and functions have not been shown or described in detail to avoid unnecessarily obscuring the description of the embodiments of the invention.

FIG. 1-A is a cross section view of an acoustic vibration sensor 100, also referred to herein as the sensor 100, under an embodiment. FIG. 2A-A is an exploded view of an acoustic vibration sensor 100, under the embodiment of FIG. 1-A. FIG. 2B-B is perspective view of an acoustic vibration sensor 100, under the embodiment of FIG. 1-A. The sensor 100 includes an enclosure 102 having a first port 104 on a first side and at least one second port 106 on a second side of the enclosure 102. A diaphragm 108, also referred to as a sensing diaphragm 108, is positioned between the first and second ports. A coupler 110, also referred to as the shroud 110 or cap 110, forms an acoustic seal around the enclosure 102 so that the first port 104 and the side of the diaphragm facing the first port 104 are isolated from the airborne acoustic environment of the human talker. The coupler 110 of an embodiment is contiguous, but is not so limited. The second port 106 couples a second side of the diaphragm to the external environment.

The sensor also includes electret material 120 and the associated components and electronics coupled to receive acoustic signals from the talker via the coupler 110 and the diaphragm 108 and convert the acoustic signals to electrical signals. Electrical contacts 130 provide the electrical signals as an output. Alternative embodiments can use any type/combination of materials and/or electronics to convert the acoustic signals to electrical signals and output the electrical signals.

The coupler 110 of an embodiment is formed using materials having acoustic impedances similar to the impedance of human skin (the characteristic acoustic impedance of skin is approximately $1.5\times10^6$ Pa×s/m). The coupler 110 therefore, is formed using a material that includes at least one of silicone gel, dielectric gel, thermoplastic elastomers (TPE), and rubber compounds, but is not so limited. As an example, the coupler 110 of an embodiment is formed using Kraiburg TPE products. As another example, the coupler 110 of an embodiment is formed using Sylgard® Silicone products.

The coupler 110 of an embodiment includes a contact device 112 that includes, for example, a nipple or protrusion that protrudes from either or both sides of the coupler 110. In operation, a contact device 112 that protrudes from both sides of the coupler 110 includes one side of the contact device 112 that is in contact with the skin surface of the talker and another side of the contact device 112 that is in contact with the diaphragm, but the embodiment is not so limited. The coupler 110 and the contact device 112 can be formed from the same or different materials.

The coupler 110 transfers acoustic energy efficiently from skin/flesh of a talker to the diaphragm, and seals the diaphragm from ambient airborne acoustic signals. Consequently, the coupler 110 with the contact device 112 efficiently transfers acoustic signals directly from the talker's body (speech vibrations) to the diaphragm while isolating the diaphragm from acoustic signals in the airborne environment of the talker (characteristic acoustic impedance of air is approximately 415 Pa×s/m). The diaphragm is isolated from acoustic signals in the airborne environment of the talker by the coupler 110 because the coupler 110 prevents the signals from reaching the diaphragm, thereby reflecting and/or dissipating much of the energy of the acoustic signals in the airborne environment. Consequently, the sensor 100 responds primarily to acoustic energy transferred from the skin of the talker, not air. When placed against the head of the talker, the sensor 100 picks up speech-induced acoustic signals on the surface of the skin while airborne acoustic noise signals are largely rejected, thereby increasing the signal-to-noise ratio and providing a very reliable source of speech information.

Performance of the sensor 100 is enhanced through the use of the seal provided between the diaphragm and the airborne environment of the talker. The seal is provided by the coupler 110. A modified gradient microphone is used in an embodiment because it has pressure ports on both ends. Thus, when the first port 104 is sealed by the coupler 110, the second port 106 provides a vent for air movement through the sensor 100. The second port is not required for operation, but does increase the sensitivity of the device to tissue-borne acoustic signals. The second port also allows more environmental acoustic noise to be detected by the device, but the device's diaphragm's sensitivity to environmental acoustic noise is significantly decreased by the loading of the coupler 110, so the increase in sensitivity to the user's speech is greater than the increase in sensitivity to environmental noise.

FIG. 3-A is a schematic diagram of a coupler 110 of an acoustic vibration sensor, under the embodiment of FIG. 1-A. The dimensions shown are in millimeters and are only intended to serve as an example for one embodiment. Alternative embodiments of the coupler can have different configurations and/or dimensions. The dimensions of the coupler 110 show that the acoustic vibration sensor 100 is small (5-7 mm in diameter and 3-5 mm thick on average) in that the sensor 100 of an embodiment is approximately the same size as typical microphone capsules found in mobile communication devices. This small form factor allows for use of the sensor 110 in highly mobile miniaturized applications, where some example applications include at least one of cellular telephones, satellite telephones, portable telephones, wireline telephones, Internet telephones, wireless transceivers, wireless communication radios, personal digital assistants (PDAs), personal computers (PCs), headset devices, head-worn devices, and earpieces.

The acoustic vibration sensor provides very accurate Voice Activity Detection (VAD) in high noise environments, where high noise environments include airborne acoustic environments in which the noise amplitude is as large if not larger than the speech amplitude as would be measured by conventional microphones. Accurate VAD information provides significant performance and efficiency benefits in a number of important speech processing applications including but not limited to: noise suppression algorithms such as the Pathfinder algorithm available from Aliph, Brisbane, Calif. and described in the Related Applications; speech compression algorithms such as the Enhanced Variable Rate Coder (EVRC) deployed in many commercial systems; and speech recognition systems.

In addition to providing signals having an improved signal-to-noise ratio, the acoustic vibration sensor uses only minimal power to operate (on the order of 200 micro Amps, for example). In contrast to alternative solutions that require power, filtering, and/or significant amplification, the acoustic vibration sensor uses a standard microphone interface to connect with signal processing devices. The use of the standard microphone interface avoids the additional expense and size of interface circuitry in a host device and supports for of the sensor in highly mobile applications where power usage is an issue.

FIG. 4-A is an exploded view of an acoustic vibration sensor 400, under an alternative embodiment. The sensor 400 includes an enclosure 402 having a first port 404 on a first side and at least one second port (not shown) on a second side of the enclosure 402. A diaphragm 408 is positioned between the first and second ports. A layer of silicone gel 409 or other similar substance is formed in contact with at least a portion of the diaphragm 408. A coupler 410 or shroud 410 is formed around the enclosure 402 and the silicon gel 409 where a portion of the coupler 410 is in contact with the silicon gel 409. The coupler 410 and silicon gel 409 in combination form an acoustic seal around the enclosure 402 so that the first port 404 and the side of the diaphragm facing the first port 404 are isolated from the acoustic environment of the human talker. The second port couples a second side of the diaphragm to the acoustic environment.

As described above, the sensor includes additional electronic materials as appropriate that couple to receive acoustic signals from the talker via the coupler 410, the silicon gel 409, and the diaphragm 408 and convert the acoustic signals to electrical signals representative of human speech. Alternative embodiments can use any type/combination of materials and/or electronics to convert the acoustic signals to electrical signals representative of human speech.

The coupler 410 and/or gel 409 of an embodiment are formed using materials having impedances matched to the impedance of human skin. As such, the coupler 410 is formed using a material that includes at least one of silicone gel, dielectric gel, thermoplastic elastomers (TPE), and rubber compounds, but is not so limited. The coupler 410 transfers acoustic energy efficiently from skin/flesh of a talker to the diaphragm, and seals the diaphragm from ambient airborne acoustic signals. Consequently, the coupler 410 efficiently transfers acoustic signals directly from the talker's body (speech vibrations) to the diaphragm while isolating the diaphragm from acoustic signals in the airborne environment of the talker. The diaphragm is isolated from acoustic signals in the airborne environment of the talker by the silicon gel 409/coupler 410 because the silicon gel 409/coupler 410 prevents the signals from reaching the diaphragm, thereby reflecting and/or dissipating much of the energy of the acoustic signals in the airborne environment. Consequently, the sensor 400 responds primarily to acoustic energy transferred from the skin of the talker, not air. When placed again the head of the talker, the sensor 400 picks up speech-induced acoustic signals on the surface of the skin while airborne acoustic noise signals are largely rejected, thereby increasing the signal-to-noise ratio and providing a very reliable source of speech information.

There are many locations outside the ear from which the acoustic vibration sensor can detect skin vibrations associated with the production of speech. The sensor can be mounted in a device, handset, or earpiece in any manner, the only restriction being that reliable skin contact is used to detect the skin-borne vibrations associated with the production of speech. FIG. 5-A shows representative areas of sensitivity 500-520 on the human head appropriate for placement of the acoustic vibration sensor 100/400, under an embodiment. The areas of sensitivity 500-520 include numerous locations 502-508 in an area behind the ear 500, at least one location 512 in an area in front of the ear 510, and in numerous locations 522-528 in the ear canal area 520. The areas of sensitivity 500-520 are the same for both sides of the human head. These representative areas of sensitivity 500-520 are provided as examples only and do not limit the embodiments described herein to use in these areas.

FIG. 6-A is a generic headset device 600 that includes an acoustic vibration sensor 100/400 placed at any of a number of locations 602-610, under an embodiment. Generally, placement of the acoustic vibration sensor 100/400 can be on any part of the device 600 that corresponds to the areas of sensitivity 500-520 (FIG. 5-A) on the human head. While a headset device is shown as an example, any number of communication devices known in the art can carry and/or couple to an acoustic vibration sensor 100/400.

FIG. 7-A is a diagram of a manufacturing method 700 for an acoustic vibration sensor, under an embodiment. Operation begins with, for example, a uni-directional microphone 720, at block 702. Silicon gel 722 is formed over/on the diaphragm (not shown) and the associated port, at block 704.

A material 724, for example polyurethane film, is formed or placed over the microphone 720/silicone gel 722 combination, at block 706, to form a coupler or shroud. A snug fit collar or other device is placed on the microphone to secure the material of the coupler during curing, at block 708.

Note that the silicon gel (block 702) is an optional component that depends on the embodiment of the sensor being manufactured, as described above. Consequently, the manufacture of an acoustic vibration sensor 100 that includes a contact device 112 (referring to FIG. 1-A) will not include the formation of silicon gel 722 over/on the diaphragm. Further, the coupler formed over the microphone for this sensor 100 will include the contact device 112 or formation of the contact device 112.

VAD Device Performance

The SSM device described above has been implemented and used in a variety of systems at Aliph. Most importantly, the SSM is a vital part of the Jawbone headset and its proper functionality is critical to the overall performance of the Jawbone headset. Without the SSM or a similar device supplying VAD information, the noise suppression performance of the Jawbone headset would be very poor.

Referring again to FIG. 1 and FIG. 2, a VAD system 102 of an embodiment includes a SSM VAD device 230 providing data to an associated algorithm 101. As detailed above, the SSM is a conventional microphone modified to prevent airborne acoustic information from coupling with the microphone's detecting elements.

During speech, when the SSM is placed on the cheek or neck, vibrations associated with speech production are easily detected. However, the airborne acoustic data is not significantly detected by the SSM. The tissue-borne acoustic signal, upon detection by the SSM, is used to generate the VAD signal in processing and denoising the signal of interest, as described above with reference to the energy/threshold method outlined in FIG. 3. This technique is used quite successfully in the Jawbone headset to determine VAD and leads to noise suppression performances similar to that shown in FIG. 4. In this Figure, plots are shown including a noisy audio signal (live recording) 402 along with a corresponding SSM-based VAD signal 404, the corresponding SSM output signal 412, and the denoised audio signal 422 following processing by the Pathfinder system using the VAD signal 404, under an embodiment. The audio signal 402 was recorded using an Aliph microphone set in a "babble" (many different human talkers) noise environment inside a chamber measuring six (6) feet on a side and having a ceiling height of eight (8) feet. The Pathfinder system is implemented in real-time, with a delay of approximately 10 msec. The difference in the raw audio signal 402 and the denoised audio signal 422 clearly show noise suppression approximately in the range of 20-25 dB with little distortion of the desired speech signal. Thus, denoising using the SSM-based VAD information is effective.

The implementation described above is a specific implementation of a VAD transducer, but the scope of this application is not so limited. There are many ways to specifically implement the ideas and techniques presented above, and the specified implementation is simply one of many that are possible.

Dynamic Audio Enhancement

Dynamic Audio Enhancement is a technique developed by Aliph to help the user better hear the person he or she is conversing with. It uses the VAD above to determine when the person is not speaking, and during that time, a long-term estimate of the environmental noise power is calculated. It also calculates an estimate of the average power of the far-end signal that the user is trying to hear. The goal is to increase intelligibility over a wide range of noise levels with respect to incoming far-end levels; that is, a wide range of signal to noise ratio: far-end speech/near-end noise. The system varies the gain of the loudspeaker and filters the incoming far-end to attain these goals.

INTRODUCTION

The DAE system comprises three stages:

1. Static high-pass filter (HP).
2. Measure of far-end and noise power levels (FL and NL).
3. Gain management (GM).

These sub-systems operate on frames of 16 samples at a time (2 ms at 8 kHz) but are not so limited. First, the far-end signal is statically filtered trough an FIR high-pass filter. Then, for each frame the FL and NL sub-systems calculate the average power level in dB, Lf or Ln respectively, to the GM sub-system. Finally, the gain management sub-system varies slowly the gain such that a specific target SNR can be attained. This gain multiplies the far-end level and provides the signal to be sent to the speaker.

High-Pass Filter

Figure 8:
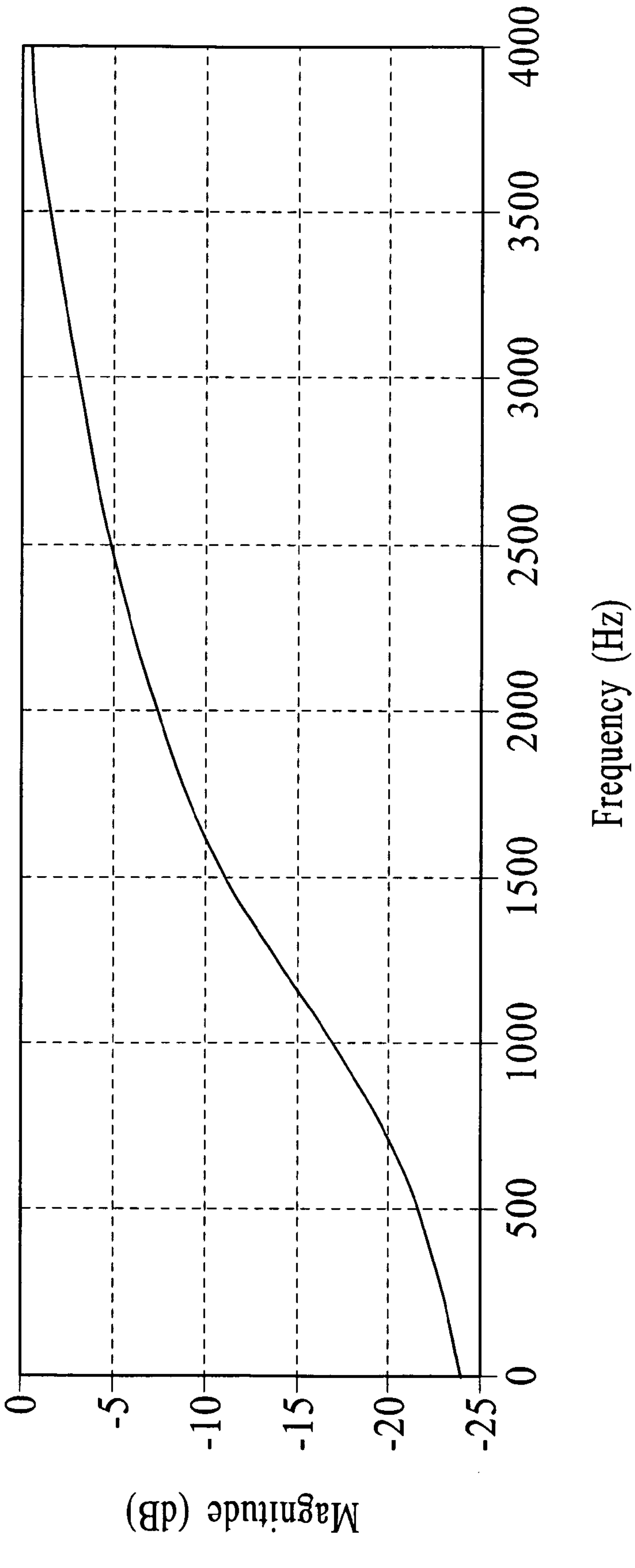
FIG. 8: Diagram of the magnitude response of the FIR highpass filter used in the DAE algorithm to increase intelligibility in high-noise acoustic environments.

It has been demonstrated that raising high frequencies of speech can improve intelligibility. We use a 33-tap high-pass FIR to do so, but are not so limited. FIG. 8 shows the frequency response of the filter used and it only attenuates the signal (the gain is always less than or equal to unity). This is in order to prevent the signal from clipping internally. The highpass filter is included in the far-end processing as soon as the system decides that the environment is loud enough to increase the gain and trigger the DAE process.

Level Measurements

Power levels are measured in the frequency range of 250 Hz-4000 Hz. They are calculated for each frame and filtered over a large number of frames (equivalent to 1 second of signal) using a cascade of two moving average (MA) filters. The moving average filter was chosen for its ability to completely "forget the past" after a period of time corresponding to the length of its impulse response, preventing large impulses from affecting for too long the system's response. Furthermore, the choice of a cascade of two filters was made where the second filter is fed with the decimated output of the first stage, guarantying low memory usage. One long MA would have required as many as 500 taps where a cascade of two requires only 25+20=45.

More specifically, once the power p is measured in the current frame and converted into a log scale (dB), it is processed by the following system:

1. Mean of p is calculated over past 25 frames once every 25 frames.
2. A delay corresponding to the duration of a long unvoiced speech is added here (for noise measure only, see below).
3. Second MA filter stage using 20 taps.

This process only takes place when the signal that is under consideration is considered to be valid:

1. For the FL sub-system: The far-end signal is speech (not comfort or other noise).
2. For the NL sub-system: The signal is environmental noise only (no near-end speech or speaker's echo present in the noise microphone).

If these constraints are not satisfied, the last valid power level is used.

A delay mechanism is implemented that removes possible unvoiced regions from the measurements (250 ms before any valid voicing frame and 200 ms after). This adds latency to the overall delay of the system and explains the delay mentioned above. In addition, since a single false positive from the VAD can freeze adaptation for as long as 450 ms, a pulse rejection technique is used as follow: a frame is declared as voiced if there was at least 20 voiced frames among the most current past 25 frames.

Concerning the far-end signal, it is obvious that the level should not be measured during silences or comfort noise. This requires us to be able to detect speech in far-end, "far-end activity", on a wide range of cell phones and volumes settings. This normally is not an issue and it is likely that a single fixed energy threshold can be used to separate comfort noise from weak speech. Otherwise, one can also use a system that ignores energies below the lowest 10% of the observed energy range for example.

Concerning the noise microphone, the problem is more challenging: It seems quite regrettable to limit noise level measures only to non-speech and non-echo frames (only around 30% of frames). However, the energy of the near-end speech in the noise microphone can be substantial, even if an LMS-based algorithm similar to Pathfinder or Pathfinder itself is used to remove the speech. Since we can't make assumption on the near-end speech intensity, it seems like we have no choice but stop measuring the noise level when near-end speech occurs.

Second, the energy of an echo from the far-end speech can be large as well but the measure is performed on the echo-cancelled signal, which can still contain an important residual echo. When measures are performed in presence of echo, it can lead the system to raise the speaker's gain G, which increases the echo, etc. This positive feedback loop is certainly not desirable. Since the gain is limited by a maximal value, it can actually start oscillating under certain conditions. There are ways around this; such as limiting the rate at which the gain can increase, but we have found the system to be much more reliable if the noise power level is only calculated when there is no near- or far-end speech taking place.

Gain Management

A cutoff is used on the incoming levels Lf and Ln in order to prevent problems at start-up:

$$Lf=\max(Lf,-60\text{ dB})$$

$$Ln=\max(Ln,-60\text{ dB})$$

The projected signal-to-noise ratio R is calculated. This is the SNR that would be reached if the gain remains unchanged:

$$R=Lf-Ln+20*\log 10(G)$$

The difference with the target SNR T is:

$$dR=R-T$$

Finally, a decision is made to change the gain if the actual SNR is too far from the target:

$$\text{If } dR<3\text{ dB, then } G=1.05*G$$

$$\text{If } dR>-3\text{ dB, then } G=0.95*G$$

Otherwise the gain remains unchanged. Also, the gain is saturated if it reaches a maximum gain limit (0 dB) or a minimum gain limit (−18 dB). This lowest limit is chosen such that it leads to a speaker's volume that is 3 dB above the level achieved when the DSP system is by-passed. Consequently, the system guaranties the volume of the speaker to increases by at least 3 dB at start-up. In fact, when the system is powered-up, G starts at the minimum value and converges to whatever gain corresponds to the desired target SNR.

Jawbone Headset

The Jawbone headset is a specific combination of the techniques and principles discussed above. It is presented as an explicit implementation of the techniques and algorithms discussed above, but the construction of a headset with the specified techniques and algorithms is not so limited to the configuration shown below. Many different configurations are possible whereby the techniques and algorithms discussed above may be implemented.

The physical Jawbone headset consists of two main components: an earpiece and a control module. The earpiece can be worn on either ear of the user. The control module, which is connected to the earpiece via a wire, can be clipped to the user's clothing during use. A unique attribute of the headset design is the design aesthetic of each component and, equally, of the two components together. These attributes are described in detail below:

- Design of "shield" (110) on earpiece (100) and control module (310) (see FIG. 1-B through 6-B)
  - The earpiece and the control module both bear a curved rectangular (brushed metal or other) metal shield. This metal shield has the effect of "shielding", or protecting the complex electronics contained behind it. It is an iconic, classic, and memorable design.
  - This "shield" on the earpiece and the control module is also accented with an off-center hole/circle on its curved surface. For the earpiece, this off-center circle represents the axis on which the shield can rotate around the earbud barrel (so the user can switch ears). On the control module, this off-center circle displays activity information when the product is in use.
  - The earpiece body, or "whale", behind the shield is designed to allow sensor interaction and is covered with soft-touch paint to reduce irritation to the user's skin during use.
- Common Design Language and Connectibility (see FIG. 3-B)
  - The design language used for the shield (110) on the earpiece (300) and the control module (310) is conspicuously similar: both components have the curved rectangular surface and the off-center circle.
  - The industrial design of the earpiece and the control module allow them to physically snap to each other for better storage and portability when the headset is not in use.

Mechanical Design

The Jawbone headset is a comfortable, bi-aural, earpiece containing a number of transducers, which is attached via a wire to a control module bearing integrated circuits for processing the transducer signals. It uses the technology described above to suppress environmental noise so that the user can be understood more clearly. It also uses a technique dubbed DAE so that the user can hear the conversation more clearly.

By virtue of its design and the signal processing technology integrated within it, this headset is comfortable and stable when worn on either ear and is able to deliver great incoming and outgoing audio quality to its user in a wide range of noise environments.

The Earpiece (FIGS. 1B through 10B)

The earpiece is made up of an earloop 120, and earbud barrel 130, and a body 240 which are connected together as one device prior to operation by user. Once assembled during manufacture, there is no requirement for the user to remove any components from the headset. The headset is intended for use on either ear, and on one ear at a time. The objective in such a design is to ensure that the headset is mechanically stable on either ear, comfortable on either ear, and the acoustic transducers are properly positioned during use.

The first mechanical design achievement is the ability for the headset to be used on either ear, without the need to remove any components. In addition, the electronic wiring that is used to connect the headset to a mobile phone or other device must be fed through the earloop 120 to ensure proper stability and comfort for the user. If this wiring is not fed through the earloop, but is rather allowed to drop directly down from the body of the earpiece, the stability of the headset can be significantly compromised. The body 240 is attached to the earbud barrel 130, around which the body is free to rotate. The "polarity" of the headset (i.e. whether it is configured for the left or right ear) is changed by rotating the body 240 through a 180° angle around the earbud barrel. Since the earloop is symmetrical along the plane of its core, the headset feels and functions in exactly the same way on both ears.

The second mechanical design achievement is the spring-loaded-body mechanism, which ensures that the body 240 is always turned inwards towards the cheek during use. This feature achieves three important requirements:

1. Slight pressure of the body 240 on the cheek enhances the overall stability and comfort of the headset during use
2. Having the body 240 against the cheek ensures that the primary microphone 710 is always pointed towards the user's mouth during use
3. Having the body 240 applied with slight pressure against the cheek ensures that the speech vibration sensor 720—a component critical to enhanced voice quality—is always in contact with the skin.

The spring-loading of the body is achieved by means of a symmetrical metal spring element 520 and a bi-polar cam 510 which together generate a torsional force between the earpiece body 810 and the earloop 500 respectively, around a rotational axis which is the earloop core. Note that the earloop is mechanically fastened to the cam, and the body is mechanically fastened to the spring. The spring is free to rotate within the cam. The metal spring is symmetrical in one axis, and the cam is symmetrical along the rotational axis, ensuring the headset behaves in exactly the same manner on each ear. When the earpiece is placed on the ear, the angle [Θ] between the earloop 820 and the body 810 is widened, forcing the cam to rotate within and against the spring. The spring provides a reactive torsional force which operates to reduce the angle [Θ] between the body 810 and the earloop 820. The body is thus always kept in contact with the user's cheek and the primary microphone 710 is always aligned toward the user's mouth.

The third mechanical design achievement is the 3-point headset mounting system, which ensures that the headset is stable and comfortable on a wide variety of ear anatomies. The first feature of this system is the semi-rigid, but elastic, earloop 820, which lightly grips the root of the pinna (see FIGS. 9-B and 10-B) through a pinching force F4 provided by its elasticity, and a compressive forced F2 provided by the spring-loading. The second feature of the system is the earbud barrel 840 which is fitted behind the tragus (or tragal notch 850) and holds the earpiece inwards through a reactive force R3 (FIG. 9-B) and provides efficient acoustic coupling of the speaker driver to the ear entry point, without occlusion. The third feature of this system is the spring-loaded body described above, which maintains pressure against the cheek during use through a compressive force F1. The result of these three features is unique earpiece stability and user comfort during use, given that the forces applied by the body and the earloop (F1 and F2, respectively) are anchored by the reactive force of the tragal notch (R3).

Applications

The Jawbone headset captures the speech and VAD information in the earpiece. This information is then routed to the control module where the VAD and noise levels are calculated and the audio from Mic1 is noise suppressed. The output of this process is a cleaned speech signal. This cleaned speech signal may be directed to any number of communications devices such as mobile phones, landline phones, portable phones, Internet telephones, wireless transceivers, personal digital assistants (PDAs), VOIP telephones, and personal computers. The control module can be connected to the communication device using wired or wireless connections. The control module can be separated from the earpiece (as in the Jawbone implementation) or can be built into the earpiece, headset, or any device designed to be worn on the body.

The invention claimed is:

1. A noise suppressing headset comprising:

an earpiece connected to a housing, wherein the earpiece is configured for wear on an ear of a user;

a microphone array in the housing, wherein a first microphone of the array is separated from a second microphone of the array by a distance, wherein acoustic noise energy of acoustic signals received by the microphone array is equivalent in each of the first microphone and the second microphone and acoustic speech energy of the acoustic signals is relatively different in each of the first microphone and the second microphone, the acoustic signals originating in an environment of the user;

an acoustic vibration sensor in the housing, the acoustic vibration sensor comprising, a protrusion that extends from the housing to contact a skin surface of the user, wherein the acoustic vibration sensor detects human tissue vibration associated with near-end speech of the user, wherein the acoustic vibration sensor comprises a diaphragm positioned adjacent a first port and a second port of the housing;

a noise suppression system executing on a processor in the housing, the processor coupled to and using signals from the microphone array and the acoustic vibration sensor to separately identify voiced speech and unvoiced speech of the acoustic signals and denoise the acoustic signals; and a dynamic audio enhancement system executing on the processor and increasing intelligibility of far-end speech, the far-end speech comprising speech received in a far-end signal from a far-end source via a communications channel coupled to the earpiece and the microphone array.

2. The system of claim 1, wherein the earpiece comprises a three-point mounting system that holds the earpiece on the user comfortably, orients the microphone array relative to a mouth of the user, and maintains the acoustic vibration sensor in contact with the skin surface.

3. The system of claim 2, wherein the three-point mounting system comprises an earloop with wires fed through the earloop, and a barrel lodged behind the tragus of the ear.

4. The system of claim 2, wherein the earpiece comprises a device adaptable for wear on either ear of the user.

5. The system of claim 1, wherein the microphone array comprises a plurality of microphones and an axis, wherein the first microphone of the array has a first vector normal to a front of the first microphone, the first vector defining the axis to be toward a mouth of a user, wherein the second microphone of the array has a second vector normal to a front of the second microphone, wherein the second vector forms an angle relative to the first vector.

6. The system of claim 5, wherein the first microphone is oriented towards a mouth of the user and the second microphone is oriented away from the mouth.

7. The system of claim 6, wherein the first microphone and the second microphone are separated by a distance in a range of approximately zero (0) centimeters to 15 centimeters.

8. The system of claim 6, wherein the angle is in a range of approximately 60 degrees to 135 degrees.

9. The system of claim 1, wherein the noise suppression system comprises denoising applications.

10. The system of claim 9, wherein the noise suppression system automatically selects at least one denoising application appropriate to data of at least one frequency subband of the acoustic signals and processes the acoustic signals using the selected denoising component to generate denoised acoustic signals.

11. The system of claim 1, wherein the denoising comprises generating a noise waveform estimate associated with noise of the acoustic signals and subtracting the noise waveform estimate from the acoustic signals when the acoustic signals includes speech and noise.

12. The system of claim 1, wherein the noise suppression system generates at least one parameter between different ones of the acoustic signals received at the microphone array.

13. The system of claim 12, wherein the at least one parameter is representative of a ratio in signal gain between portions of the acoustic signals.

14. The system of claim 12, wherein the parameter comprises a ratio of a gain of the first microphone and a gain of the second microphone.

15. The system of claim 12, wherein the noise suppression system:

considers a magnitude of the parameter over time in view of a predetermined threshold; and identifies information of the acoustic signals as unvoiced speech when a difference between a parameter of the different ones of the acoustic signals exceeds a first threshold.

16. The system of claim 15, wherein the noise suppression system identifies information of the acoustic signals as voiced speech when the difference exceeds a second threshold.

17. The system of claim 1, comprising a coupler that couples a first set of signals to a first side of the diaphragm and rejects a second set of signals by isolating the diaphragm from the second set of signals, wherein the coupler includes an internal protrusion on a first side of the coupler that couples to the first side of the diaphragm, wherein the rear port couples a second side of the diaphragm to the environment.

18. The system of claim 17, wherein the coupler includes the protrusion, and the first set of signals include speech signals of the user and the second set of signals include noise of the environment.

19. The system of claim 17, wherein the coupler comprises a material with an impedance matching an impedance of human skin.

20. The system of claim 1, wherein the dynamic audio enhancement system:

generates an average power estimate of a far-end signal received via the communications channel, the far-end signal comprising the far-end speech;

generates a noise power estimate of the environment;

generates a signal-to-noise ratio (SNR) as a ratio of the average power estimate to the noise power estimate;

controls a gain of the earpiece in response to the SNR.

21. The system of claim 20, comprising a voice activity detection (VAD) device.

22. The system of claim 21, wherein the dynamic audio enhancement system generates the noise power estimate in the absence of user speech as determined using the VAD device.

23. The system of claim 21, wherein the VAD device comprises at least one of the acoustic vibration sensor and a skin surface microphone (SSM) device.

24. The system of claim 20, wherein the control of the gain of the earpiece comprises varying the gain to attain a target SNR.

25. The system of claim 20, wherein the control of the gain comprises at least one of increasing a gain of the far-end signal and decreasing a gain of the far-end signal.

26. The system of claim 25, wherein the control of the gain comprises increasing the gain of frequency components greater than 2 kilohertz.

27. The system of claim 25, wherein the control of the gain comprises increasing the gain by a factor in a range of approximately 1.4 to 2.

* * * * *